United States Patent [19]

Chakravarty et al.

[11] Patent Number: 5,250,558
[45] Date of Patent: Oct. 5, 1993

[54] SUBSTITUTED TRIAZOLINONES, TRIAZOLINETHIONES, AND TRIAZOLINIMINES AS NEUROTENSIN ANTAGONISTS USED TO TREAT PSYCHOSIS

[75] Inventors: Prasun K. Chakravarty, Edison, N.J.; Richard W. Ransom, New Britian, Pa.

[73] Assignee: Merck & Co., Inc., Rahway, N.J.

[21] Appl. No.: 826,704

[22] Filed: Jan. 28, 1992

[51] Int. Cl.$^5$ ............... A61K 31/41; A61K 31/34; A61K 31/40; A61K 31/445
[52] U.S. Cl. ................ 514/383; 514/384; 514/315; 514/336; 514/343; 514/461; 514/465; 514/408; 514/427; 514/329; 514/330
[58] Field of Search ............ 514/381, 382, 383, 384, 514/408

[56] References Cited

U.S. PATENT DOCUMENTS

| | | | |
|---|---|---|---|
| 4,425,269 | 1/1984 | Christy et al. | 260/112.50 R |
| 4,439,359 | 3/1984 | Holly et al. | 260/112.50 R |
| 5,100,910 | 3/1992 | Milcent et al. | 514/381 |
| 5,137,902 | 8/1992 | Carini | 514/381 |
| 5,137,906 | 8/1992 | Chiu et al. | 514/381 |

FOREIGN PATENT DOCUMENTS

| | | |
|---|---|---|
| 412594 | 2/1991 | European Pat. Off. |
| 452926 | 10/1991 | European Pat. Off. |
| 0477049A1 | 3/1992 | France |

OTHER PUBLICATIONS

"Sanofi presents novel products", Scrip World Pharmaceutical News, Dec. 4, 1992, No. 1776.

deQuidt et al, "Neutrotensin facilitates dopamine release in vitro from rat striatal slices", Brain Research, 274, (1983), 376–380.

Shi et al, "Roles of Intracellular cAMP and Protein Kinase A in the Actions of Dopamine...", J. of Neuroscience, Jun. 1992, 12(6): 2433-2438.

Szigethy et al, "Correspondence Between High Affinity 125 I-Neurotensin Binding Sites...", J. of Comp. Neurology 279: 128-137 (1989).

(List continued on next page.)

Primary Examiner—Frederick E. Waddell
Assistant Examiner—T. I. Criares
Attorney, Agent, or Firm—Valerie J. Camara; William H. Nicholson; Joseph F. DiPrima

[57] ABSTRACT

Substituted triazolinone, triazolinethione, and triazolinimine compounds of formula (I) are as neurotensin II antagonists. These compounds have the general formula:

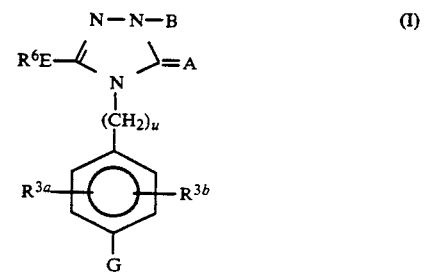

wherein G is $R^1$ or $R^{2a}$—

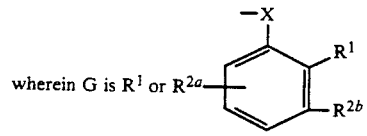

7 Claims, No Drawings

OTHER PUBLICATIONS

Kitabgi, "Neurotensin Modulates Dopamine Neurotransmission at Several Levels . . . ", Neurochem Int., vol. 14, No. 2, pp. 111–119 (1989).

Blaha et al, "Effects of Neurotensin on Dopamine Release and Metabilish in the Rat Striatum . . . ", Neuroscience, vol. 34, No. 3, pp. 699–705 (1990).

Palacios et al, "Neurotensin receptors are located on dopamine-containing neurones in rat midbrain", Nature, vol. 294, Dec. 10, 1981, pp. 587–589.

Glimcher et al, "Neurotensin self-injection in the ventral tegmental area", Strain Research, 403, (1987), pp. 147–150.

Stoessl et al, "Neurotensin and neurotensin analogues modify the effect of chronic neuroleptic . . . ", Strain Research, 558, (1991), pp. 289–295.

Rompre et al, "Faciliration of brain stimulation reward by mesencephalic injections . . . ", European J. of Pharm., 211 (1992), pp. 295–303.

Prange et al, "The Manifold Actions of Neurotensin: A First Synthesis", NYAS, pp. 368–375, (1982).

G. A. Cain, et al. Neurotensin Based Analgesics: 203rd National Meeting of the Am. Chem. Soc. Apr. 5–10, (1992).

SUBSTITUTED TRIAZOLINONES, TRIAZOLINETHIONES, AND TRIAZOLINIMINES AS NEUROTENSIN ANTAGONISTS USED TO TREAT PSYCHOSIS

INTRODUCTION OF THE INVENTION

This invention is concerned with a method of treating disease states mediated by neurotensin by the administration to a patient in need of treatment of a theraputically effective amount of a neurotensin antagonist which is a substituted triazolinone, triazolinethione and triazolinimine compound of structural formula I:

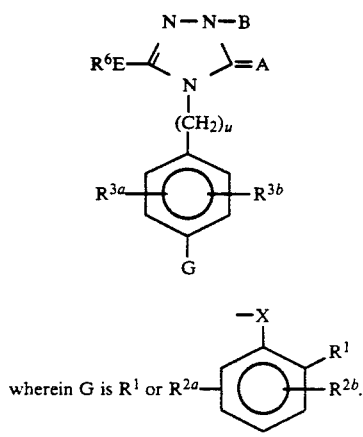

As neurotensin antagonists these compounds find utility in the treatment of CNS dysfunctions such as psychoses, depression, cognitive dysfunction, such as Alzheimer's disease, anxiety, tardive dyskinesia, drug dependency, panic attack and mania. The neurotensin antagonist property also imparts to the compounds utility in GI disorders such as gastroesophageal reflux disorder (GERD), irritable bowel syndrome, diarrhea, cholic, ulcer, GI tumors, dyspepsia, pancreatitis, esophagitis and gastroparesis. The known ability of neurotensin to release mast cell histamine indicates that antagonists will be useful in the treatment of allergic and inflammatory conditions.

BACKGROUND OF THE INVENTION

Neurotensin (NT) is a tridecapeptide hormone (pGlu-Leu-Tyr-Glu-Asn-Lys-Pro-Arg-Arg-Pro-Tyr-Ile-Leu-OH), originally isolated from the bovine hypothalamus [Carraway, R. and Leeman, S. E., *J. Biol. Chem.*, 248, 6854 (1973)], has subsequently been shown to be distributed in the brain [Uhl, G. R., et al., *Proc. Natl. Acad. Sci. USA*, 74, 4059–4063 (1977),] gastrointestinal tract [1). Kitabgi, P., Carraway, R. and Leeman, S. E., *J. Biol. Chem.*, 251, 7053 (1976); 2). Carraway, R., Kitabgi, P., and Leeman, S. E., *J. Biol. Chem.*, 253, 7996 (1978); 3). Helmstadler, V., Taugner, C., Feurle, G. E. and Frossman, W. G., *Histochemistry*, 53, 35–41 (1977)] and pancreas [Feurle, G. E. and Niestroj, S., *Pancreas*, 6, 202–207 (1991) and references cited therein] of various animals including human [Mai, J. K., et al., *Neuroscience*, 22, 499–524 (1987)]. Although the physiological roles of neurotensin are not as of yet completely understood, this endogenous peptide participates in a wide spectrum of central [1). Prange, A. J. and Nemeroff, C. B., *Annal. N.Y. Acad. Sciences*, 400, 368–375 (1982); 2). Stowe, Z. N. and Nemeroff, C. B., *Life Sci.*, 49, 987–1002, (1991); 3) Kitabgi, P., *Neurochem. Int.*, 14, 111–119 (1989); 4). Levant and Nemeroff, C. B., Current topics in *Neuroendocrinology*, 8, 231–262 (1988)] and peripheral [Leeman, S. E., Aronin, N. and Ferris, C., *Hormone Res.*, 38, 93–132 (1982)] biological functions.

Neurotensin is also known to release mast cell histamine, indicating that antagonists will be useful in the treatment of allergic and inflammatory conditions, as well. [See, Rossei, S. S. and Miller, R. J., *Life Sci.*, 31, 509–516 (1982) and Kurose, M. and Saeki, K., *Eur. J. Pharmacol.*, 76, 129–136 (1981).]

Neurotensin, like most other peptides, is unable to cross the blood-brain barrier (BBB). However, certain peripheral effects of neurotensin have been observed after central administration of the peptide [Prange, A. J. and Nemeroff, C. B., *Annal. N.Y. Acad. Sciences*, 400, 368–391 (1982). The direct application of neurotensin into the brain causes hypothermia, potentiation of barbiturate induced sedation, catalepsy, antinociception, blockade of psychostimulant-induced locomotor activity and reduced food consumption. In the central nervous system (CNS), neurotensin behaves as a neurotransmitter or neuromodulator [1) Uhl, G. R. and Snyder, S. H., *Eur. J. Pharmacol.*, 41, 89–91 (1977); 2) Uhl, G. R., *Annal. N.Y. Acad. Sciences*, 400, 132–149 (1982)], and has been shown to have close anatomical and biochemical associations with the dopaminergic (DA) system [Nemeroff, C. B., et al. *Annal. N.Y. Acad. Sciences*, 400, 330–344 (1982)]. Neurotensin increases the synthesis and the turnover of DA in rat brain. Acute and chronic treatment with clinically efficacious antipsychotic drugs (e.g., haloperidol, chloropromazine) have consistently demonstrated an increase in neurotensin concentrations in the nucleus accumbens and striatum while phenothiazines that are not antipsychotics did not produce this increase. Behaviorally, neurotensin, after central administration, mimics the effects of systemically administered neuroleptics. However, unlike classical neuroleptics (which primarily acts on $D_2$ receptors), neurotensin fails to bind to dopamine receptors or inhibit cAMP accumulation following DA receptor activation. Neurotensin does not block the stereotypy induced by DA agonists. The post-mortem studies of patients with schizophrenia showed an increase in the level of neurotensin in the Brodman's area 32 of human brain [Nemeroff, C. B., et. al., *Science.*, 221, 972–975 (1983) and references cited therein], which suggest possible roles of neurotensin in the pathophysiology of this disease. Neurotensin receptors have also been implicated in Parkinson's disease and progressive supranuclear palsy [Chinaglia, G. et al., *Neuroscience*, 39, 351–360 (1990)].

Of the total body neurotensin in many mammalian species, more than 80% is present in the gastrointestinal tract, especially in the distal small intestine in the endocrine like N-cells. In the gut, neurotensin stimulates pancreatic secretion [Sakamoto, T., et al., *Surgery*, 96, 146-53 (1984)], inhibits gastric acid secretion and gastric emptying [Blackburn, A. M., *Lancet*, 1, 987–989 (1980)]. Neurotensin also stimulates the growth of small intestinal mucosa in an isolated defunctional loop of jejunum, which suggests a direct systemic effect of neurotensin in the gut. In addition, neurotensin can stimulate pancreatic exocrine secretion in mammals [Iwatsuki, K., et al., *Clin. Expt. Pharmacol. Physiol.*, 18, 475–481 (1991) and references cited therein].

From the structural work, it is evident that the biological activity of neurotensin resides within the carboxy terminal five or six amino acid residues. The C-terminal hexapeptide NT[8-13] has displayed full biological activity of the tridecapeptide. In contrast, all amino terminal partial sequences are essentially inactive [Leeman, S. E. and Carraway, R. E., *Annal. N.Y. Acad. Sciences*, 400, 1–16 (1982)]. The C-terminal COOH group and two Arg residues are essential for the biological activity of NT[8-13] as well as neurotensin. L-amino acids are required at positions-9, 10, 11 and 13, and only Arg[8] can be replaced by D-Arg without loss of any activity. At the position-11, an aromatic amino acid is essential. Similarly, alkyl side-chains of Ile[12] and Leu[13] are also necessary for full biological activity [Kitabgi, P., *Annal. N.Y. Acad. Sciences*, 400, 37–53 (1982)]. Most of the analogues of neurotensin examined generally behaved as agonists. However, two analogues D-Trp[11]-NT and Tyr(Me)[11]-NT have displayed partial antagonist activity [Rioux, F. R., et al., *Eur. J. Pharmacol.*, 66, 373–379 (1980)].

The compounds in the novel method of treatment of this invention are known in the art, having been disclosed in U.S. Ser. No. 07/504,507 filed Apr. 4, 1990 and in the corresponding published European Patent Application EP 412, 594 (Merck & Co., Inc.) on Feb. 13, 1991 where they are alleged to be angiotensin II receptor antagonists useful in the treatment of hypertension and ocular hypertension.

Although there are reports of peptidic neurotensin antagonists, they are unstable and not orally active and none are clinically available. There are no reports of non-peptidic neurotensin antagonists.

Now with this invention there are provided non-peptidic neurotensin antagonists.

DETAILED DESCRIPTION OF THE INVENTION

The compounds useful in the novel method of treatment of this invention have structural formula (I):

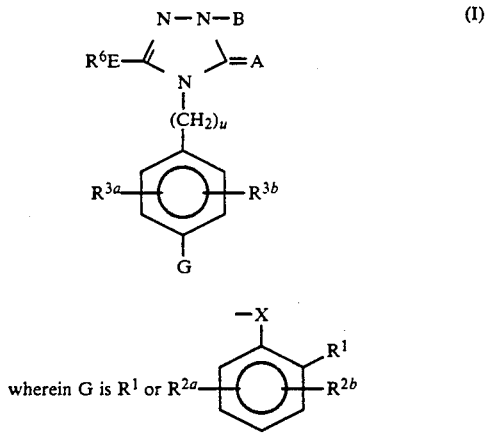

or a pharmaceutically acceptable salt thereof, wherein:

$R^1$ is
(a) —NHSO$_2$R$^{23}$,
(b) —NHSO$_2$NHCOR$^{23}$,
(c) —NHCONHSO$_2$R$^{23}$,
(d) —SO$_2$NHR$^{23}$,
(e) —SO$_2$NHCOR$^{23}$,
(f) —SO$_2$NHCONR$^{24}$R$^{23}$,
(g) —SO$_2$NHCOOR$^{23}$,
(h) —SO$_2$NHOR$^{23}$,
(i) —CH$_2$SO$_2$NHCOR$^{23}$,
(j) —CH$_2$SO$_2$NHCONHR$^{23}$,
(k) —CO$_2$H, or
(l) —1H-tetrazol-5-yl;

$R^{2a}$ and $R^{2b}$ are each independently:
(a) hydrogen,
(b) —Cl, —Br, —I, or —F,
(c) —CF$_3$,
(d) C$_1$-C$_4$-alkyl, or
(e) C$_1$-C$_4$-alkoxy;

$R^{3a}$ is
(a) —H,
(b) —Cl, —Br, —I, or —F,
(c) C$_1$-C$_6$-alkyl,
(d) C$_1$-C$_6$-alkoxy, or
(e) C$_1$-C$_6$-alkoxy-C$_1$-C$_4$-alkyl;

$R^{3b}$ is
(a) —H,
(b) —Cl, —Br, —I, or —F,
(c) C$_1$-C$_6$-alkyl,
(d) C$_1$-C$_5$-alkylcarbonyloxy,
(e) C$_1$-C$_6$-alkoxy, or
(f) —CF$_3$;

$R^4$ is H, C$_1$-C$_6$-alkyl, —CH$_2$-aryl or aryl, wherein aryl is phenyl or naphthyl unsubstituted or substituted with one or two substituents selected from the group consisting of: —Cl, —Br, —I, —F, C$_1$-C$_4$-alkyl, C$_1$-C$_4$-alkoxy, NO$_2$, CF$_3$, C$_1$-C$_4$-alkylthio, —OH, —NH$_2$, —CO$_2$H, —CO$_2$—C$_1$-C$_4$alkyl, —CN and —NHCOR$^9$;

$R^5$ is H or —CH(R$^4$)—O—CO—R$^{4a}$, wherein R$^{4a}$ is C$_1$-C$_6$-alkyl, aryl or —CH$_2$-aryl;

E is a single bond, —NR$^{13}$(CH$_2$)$_s$—, —S(O)$_x$(CH$_2$)$_s$— where x is 0 to 2 and s is 0 to 5, —CH(OH)—, —O(CH$_2$)$_s$—, —CO—;

$R^6$ is
(a) phenyl unsubstituted or substituted with 1 or 2 substituents selected from the group consisting of: Cl, Br, I, or F, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, C$_3$-C$_7$-cycloalkyl, and C$_3$-C$_{10}$-alkenyl;
(b) C$_1$-C$_6$-alkyl, C$_2$-C$_6$-alkenyl or C$_2$-C$_6$-alkynyl each of which is unsubstituted or substituted with one or more substituents selected from the group consisting of: aryl, C$_3$-C$_7$-cycloalkyl, Cl, Br, I, F, —OH, —O—C$_1$-C$_4$-alkyl, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and —S—C$_1$-C$_4$-alkyl;
(c) an unsubstituted, monosubstituted or disubstituted aromatic 5- or 6-membered ring which can contain one or two heteroatoms selected from the group consisting of N, O, and S, and wherein the substituents are members selected from the group consisting of —OH, —SH, C$_1$-C$_4$-alkyl, C$_1$-C$_4$-alkyloxy, —CF$_3$, Cl, Br, I, F, and NO$_2$;
(d) mono-, di-, tri- or polyfluoro-C$_1$-C$_5$-alkyl;
(e) C$_3$-C$_7$-cycloalkyl, unsubstituted or substituted with one or more substituents selected from the group consisting of: C$_1$-C$_4$-alkyl, O—C$_1$-C$_4$-alkyl, S—C$_1$-C$_4$-alkyl, OH, perfluoro-C$_1$-C$_4$-alkyl, or Cl, Br, F, and I;
(f) C$_3$-C$_7$-cycloalkyl-C$_1$-C$_3$-alkyl wherein the cycloalkyl is unsubstituted or substituted as in (e) above;

A is =O, =S or =NR$^{21}$;

B is
(a) H provided A is not NR$^{21}$, (b) $C_1$–$C_{10}$-alkyl;
(c) substituted $C_1$–$C_{10}$-alkyl in which one or more substituent(s) is selected from the group consisting of:
  (1) I, Br, Cl, or F,
  (2) hydroxy,
  (3) $C_1$–$C_{10}$-alkoxy,
  (4) $C_1$–$C_5$-alkoxycarbonyl,
  (5) $C_1$–$C_4$-alkylcarbonyloxy,
  (6) $C_3$–$C_8$-cycloalkyl,
  (7) phenyl, naphthyl or biphenyl,
  (8) substituted phenyl, naphthyl or biphenyl wherein the substituents are $V_1$, $V_2$, $V_3$, $V_4$ and $V_5$,
  (9) $C_1$–$C_{10}$-alkyl-$S(O)_p$ in which p is 0 to 2,
  (10) $C_3$–$C_8$-cycloalkyl-$S(O)_p$,
  (11) phenyl-$S(O)_p$,
  (12) substituted phenyl-$S(O)_p$ in which the substituents are $V_1$–$V_5$,
  (13) oxo,
  (14) carboxy,
  (15) $NR^9R^9$,
  (16) $C_1$–$C_5$-alkylaminocarbonyl,
  (17) di($C_1$–$C_5$-alkyl)aminocarbonyl,
  (18) cyano,
  (19) —$OCONR^{21}R^{22}$,
  (20) —$NR^{21}COR^{22}$,
  (21) —$NR^{21}CO_2R^{22}$,
  (22) —$NR^{21}CONR^{21}R^{22}$,
  (23) —$NR^{21}CON(CH_2CH_2)_2L$
  (24) —$OCON(CH_2CH_2)_2L$, wherein L is a single bond, $CH_2$, O, $S(O)_p$ or $NR^9$,
(d) $C_2$–$C_{10}$-alkenyl,
(e) $C_2$–$C_{10}$-alkynyl,
(f) $C_3$–$C_8$-cycloalkyl,
(g) substituted $C_3$–$C_8$-cycloalkyl or substituted $C_3$–$C_8$-cycloalkyl-$C_1$–$C_4$-alkyl having one or more substituents selected from the group consisting of:
  (1) Cl, Br, F, or I,
  (2) hydroxy,
  (3) $C_1$–$C_6$-alkyl,
  (4) $C_1$–$C_6$-alkoxy,
  (5) $C_1$–$C_4$-alkylcarbonyloxy,
  (6) $C_1$–$C_5$-alkoxycarbonyl,
  (7) carboxy,
  (8) oxo,
  (9) $C_1$–$C_5$-alkylaminocarbonyl,
  (10) di($C_1$–$C_5$-alkyl)aminocarbonyl
  (11) $C_1$–$C_4$-alkylcarbonyl;
  (12) phenyl, naphthyl or biphenyl,
  (13) substituted phenyl, naphthyl or biphenyl in which the substituents are $V_1$, $V_2$, $V_3$, $V_4$ and $V_5$,
  (14) —$NR^{21}COR^{22}$,
  (15) —$NR^{21}CO_2R^{22}$,
  (16) —$OCONR^{21}R^{22}$, and
  (17) —CN;
(h) phenyl, naphthyl, or biphenyl,
(i) substituted phenyl, naphthyl, or biphenyl in which the substituents are $V_1$, $V_2$, $V_3$, $V_4$ and $V_5$,
(j) phenyl-$(CH_2)_r$—$(Q)_c$—$(CH_2)_r$—,
(k) substituted phenyl-$(CH_2)_r$—$(Q)_c$—$(CH_2)_r$— in which the phenyl group is substituted with $V_1$, $V_2$, $V_3$, $V_4$ and $V_5$, or
(l) heterocycle-$(CH_2)_r$—$(Q)_c$—$(CH_2)_r$—, wherein the heterocycle is 5- or 6-membered containing one or two heteroatoms such as pyridine, furan, pyrrole, imidazole or thiazole and unsubstituted or substituted with $V_1$ and $V_2$;

$R^9$ is H, $C_1$–$C_5$-alkyl, aryl or —$CH_2$-aryl;
$R^{10}$ is H, $C_1$–$C_4$-alkyl, or
$R^9$ and $R^{10}$ together can be —$(CH_2)_m$— where m is 3–6;
$R^{11}$ is H, $C_1$–$C_6$-alkyl, $C_2$–$C_4$-alkenyl, $C_1$–$C_4$-alkoxy-$C_1$–$C_4$-alkyl, or —$CH_2$–$C_6H_4R^{20}$;
$R^{12}$ is —CN, —$NO_2$ or —$CO_2R^4$;
$R^{13}$ is H, $C_2$–$C_4$-alkanoyl, $C_1$–$C_6$-alkyl, allyl, $C_3$–$C_6$-cycloalkyl, phenyl or benzyl;
$R^{14}$ is H, $C_1$–$C_8$-alkyl, $C_1$–$C_8$-perfluoroalkyl, $C_3$–$C_6$-cycloalkyl, phenyl or benzyl;
$R^{15}$ is H, $C_1$–$C_6$-alkyl, hydroxy;
$R^{16}$ is H, $C_1$–$C_6$-alkyl, $C_3$–$C_6$-cycloalkyl, phenyl or benzyl;
$R^{17}$ is —$NR^9R^{10}$, —$OR^{10}$, —$NHCONH_2$, —$NHCSNH_2$, —$NHSO_2CF_3$,

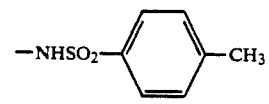

or

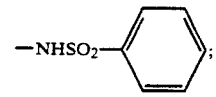;

$R^{18}$ and $R^{19}$ are independently $C_1$–$C_4$-alkyl or taken together are —$(CH_2)_q$— where q is 2 or 3;
$R^{20}$ is H, —$NO_2$, —$NH_2$, —OH or —$OCH_3$;
$R^{21}$ is
  (a) H,
  (b) phenyl, unsubstituted or substituted with 1 or 2 substituents selected from the group consisting of: Cl, Br, I, or F, —O—$C_1$–$C_4$-alkyl, $C_1$–$C_4$-alkyl, —$NO_2$, —$CF_3$, —$SO_2NR^9R^{10}$, —S—$C_1$–$C_4$-alkyl, —OH, —$NH_2$, —$COOR^4$, $C_3$–$C_7$-cycloalkyl, and $C_3$–$C_{10}$-alkenyl;
  (c) $C_1$–$C_6$-alkyl, $C_2$–$C_6$-alkenyl or $C_2$–$C_6$-alkynyl each of which is unsubstituted or substituted with one or more substituents selected from the group consisting of aryl, $C_3$–$C_7$-cycloalkyl, Cl, Br, I, F, —OH, —O—$C_1$–$C_4$-alkyl, —$NH_2$, —$NH(C_1$–$C_4$-alkyl), —$N(C_1$–$C_4$-alkyl)$_2$, —$NH$—$SO_2R^4$, —$COOR^4$, —$SO_2NHR^9$, and —S—$C_1$–$C_4$-alkyl;
  (d) an unsubstituted, monosubstituted or disubstituted aromatic 5 or 6 membered ring comprising one or two heteroatoms selected from the group consisting of N, O, and S, and wherein the substituents are members selected from the group consisting of: —OH, —SH, $C_1$–$C_4$-alkyl, $C_1$–$C_4$-alkyloxy, —$CF_3$, —$COOR^4$, Cl, Br, I, F, and $NO_2$; or
  (e) $C_3$–$C_7$-cycloalkyl unsubstituted or substituted with one or more substituents selected from the group consisting of: $C_1$–$C_4$-alkyl, —O—$C_1$–$C_4$-alkyl, —S—$C_1$–$C_4$-alkyl, —OH, —$COOR^4$, $C_1$–$C_4$-perfluoroalkyl, Cl, Br, F, and I, or
  (f) ($C_1$–$C_4$)-perfluoroalkyl;
$R^{22}$ is $R^{21}$, excluding H;
$R^{23}$ is
  (a) aryl,
  (b) heteroaryl is an unsubstituted, monosubstituted or disubstituted 5- or 6-membered aromatic ring, such as thiazole, imidazole, pyrazole oxazole pyridine, thiazone pyrazine pyrimidine or the like, which contains from 1 to 3 heteroatoms selected from the group consisting of O, N and S and wherein the substituents are members selected from the group consisting of —OH, —SH, $C_1$-$C_4$-alkyl, $C_1$-$C_4$-alkoxy, —$CF_3$, Cl, Br, F, I, —$NO_2$, —$CO_2H$, —$CO_2$—$C_1$-$C_4$-alkyl, —$NH_2$, —NH($C_1$-$C_4$-alkyl) and —N($C_1$-$C_4$-alkyl)$_2$;

(c) $C_3$-$C_7$-cycloalkyl unsubstituted or substituted with one or more substituents selected from the group consisting of: $C_1$-$C_4$-alkyl, —O—$C_1$-$C_4$-alkyl, —S—$C_1$-$C_4$-alkyl, —OH, —$COOR^4$, perfluoro-$C_1$-$C_4$-alkyl, Cl, Br, F, and I;

(d) $C_1$-$C_8$-alkyl unsubstituted or substituted with one or two substituents selected from the group consisting of: aryl, heteroaryl, —OH, —SH, $C_1$-$C_4$-alkyl, $C_2$-$C_4$-alkenyl, $C_2$-$C_4$-alkynyl —O($C_1$-$C_4$-alkyl), S($C_1$-$C_4$-alkyl), —$C_3$-$C_8$-cycloalkyl, —$CF_3$, Cl, Br, F, I, —$NO_2$, —$CO_2H$, —$CO_2$—$C_1$-$C_4$-alkyl, —$PO_3H$, —PO(OH)(O—$C_1$-$C_4$-alkyl), —PO($OR^4$)($R^9$), —$NH_2$, —NH($C_1$-$C_4$-alkyl), —N($C_1$-$C_4$-alkyl)$_2$, NH-aryl, N-(aryl)$_2$, —N($CH_2CH_2$)$_2$L, —$NR^4COR^{22}$, —$CONR^4R^{22}$, —$OCONR^4R^{22}$, —$SO_2NR^4R^{22}$, —$NR^4SO_2R^{22}$, (e) polyfluoro-$C_1$-$C_4$-alkyl, (f) —$NR^{21}R^{21}$, or, (g) —N($CH_2CH_2$)$_2$L;

L is a single bond, $CH_2$, O, $S(O)_p$, or $NR^9$;

$R^{24}$ is
(a) H,
(b) aryl,
(c) heteroaryl, or
(d) $C_1$-$C_6$-alkyl substituted or unsubstituted with aryl;

X is
(a) a single bond,
(b) —CO—,
(c) —O—,
(d) —S—, (e) 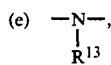

(f) 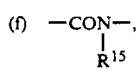

(g) 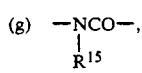

(h) —$OCH_2$—,
(i) —$CH_2O$—,
(j) —$SCH_2$—,
(k) —$CH_2S$—,
(l) —$NHC(R^9)(R^{10})$—,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—,
(v) 1,1-dimethylcyclopropyl or 1,2-dimethylcyclopropyl;

(w) 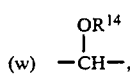

(x) 

(y) 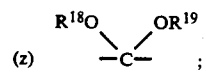

or (z) $\begin{matrix} R^{18}O & OR^{19} \\ \diagdown & \diagup \\ & -C- \end{matrix}$ ;

Q is —C(O)—, —S—, —O— or —$NR^4$;

c is 0 or 1;

r and t are 0 to 2;

$V_1$, $V_2$, $V_3$, $V_4$ and $V_5$ are each independently selected from:
(a) H,
(b) $C_1$-$C_5$-alkoxy,
(c) $C_1$-$C_5$-alkyl,
(d) hydroxy,
(e) $C_1$-$C_5$-alkyl-$S(O)_p$,
(f) —CN,
(g) —$NO_2$,
(h) —$NR^9R^{10}$,
(i) $C_1$-$C_5$-alkyl-$CONR^9R^{10}$,
(j) —$CONR^9R^{10}$,
(k) —$CO_2R^9$,
(l) $C_1$-$C_5$-alkyl-carbonyl,
(m) $CF_3$,
(n) I, Br, Cl, F,
(o) hydroxy-$C_1$-$C_4$-alkyl-,
(p) carboxy-$C_1$-$C_4$-alkyl-,
(q) -1H-tetrazol-5-yl,
(r) —NH—$SO_2CF_3$,
(s) aryl,
(t) $C_1$-$C_5$-alkyl-$CO_2R^9$,
(u) aryloxy,
(v) aryl-$C_1$-$C_3$-alkoxy,
(w) aryl-$C_1$-$C_3$-alkyl,
(x) carboxyphenyl,
(y) heteroaryl,
(z) 2-oxazolin-2-yl optionally bearing one or more $C_1$-$C_4$-alkyl substituents,
(aa) —$(CH_2)_tOCOR^{22}$,
(bb) —$(CH_2)_tOCONR^{21}R^{22}$,
(cc) —$(CH_2)_tNR^{21}COR^{22}$,
(dd) —$(CH_2)_tNR^{21}CO_2R^{22}$,
(ee) —$(CH_2)_tNR^{21}CONR^{21}R^{22}$,
(ff) —$(CH_2)_tNR^{21}CON(CH_2CH_2)_2L$,
(gg) —$(CH_2)_tOCON(CH_2CH_2)_2L$,
(hh) —$N(CH_2CH_2)_2L$,
(ii) —$C_1$-$C_5$-alkyl-$CON(CH_2CH_2)_2L$,
(jj) —$CON(CH_2CH_2)L$;

u is 1 or 2; and

Z is O, $Nr^{13}$ or S.

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl. The term "halo" means Cl, Br, I or F.

One embodiment of the compounds of Formula (I) are those compounds wherein:

$R^1$ is (a) —NHSO$_2$R$^{23}$,
(b) —NHSO$_2$NHCOR$^{23}$,
(c) —NHCONHSO$_2$R$^{23}$,
(d) —SO$_2$NHR$^{23}$,
(e) —SO$_2$NHCOR$^{23}$,
(f) —SO$_2$NHCONR$^{24}$R$^{23}$,
(g) —SO$_2$NHCOOR$^{23}$,
(h) —SO$_2$NHOR$^{23}$,
(i) —CH$_2$SO$_2$NHCOR$^{23}$,
(j) —CH$_2$SO$_2$NHCONHR$^{23}$, or
(k) -1H-tetrazol-5-yl;

R$^{2a}$ is H;
R$^{2b}$ is H, F, Cl, CF$_3$ or C$_1$–C$_4$-alkyl;
R$^{3a}$ is H;
R$^{3b}$ is H, F, Cl, CF$_3$, C$_1$–C$_4$-alkyl, C$_1$–C$_4$-alkoxy, C$_1$–C$_4$-alkylthio, —SO$_2$—CH$_3$, NH$_2$, —N(C$_1$–C$_4$-alkyl)$_2$ or —NO$_2$;
E is a single bond, —O— or —S—;
R$^6$ is
  (a) C$_1$–C$_6$-alkyl unsubstituted or substituted with a substituent selected from the group consisting of: Cl, F, CF$_3$, —OH, —O—CH$_3$, —OC$_2$H$_5$, —S—CH$_3$, —S—C$_2$H$_5$, phenyl, cyclopropyl, or C$_1$–C$_2$-alkylcyclopropyl;
  (b) C$_2$–C$_6$-alkenyl or C$_2$–C$_6$-alkynyl;
  (c) phenyl unsubstituted or substituted with Cl, F, Br, I, —CF$_3$, —NO$_2$, —OH, —NH$_2$, —S—CH$_3$, —S—C$_2$H$_5$, —SO$_2$NH$_2$, —O—CH$_3$;
  (d) a heteroaryl which is a member selected from the group consisting of 2-pyridyl, 4-pyridyl, 2-pyrimidyl, 4-pyrimidyl, imidazolyl, thiazolyl, thienyl, or furyl,
  (e) perfluoro-C$_1$–C$_4$-alkyl which is a member selected from the group consisting of CF$_3$—, CF$_3$CF$_2$—, CF$_3$CF$_2$CF$_2$—, or CF$_3$CF$_2$CF$_2$CF$_2$—;
  (f) C$_3$–C$_7$-cycloalkyl unsubstituted or substituted with methyl, ethyl, CF$_3$ or CF$_3$CF$_2$;
A is =O, =S or =NR$^{21}$;
B is
  (a) H provided A is not NR$^{21}$,
  (b) C$_1$–C$_{10}$-alkyl,
  (c) substituted C$_1$–C$_{10}$-alkyl in which one or two substituents are selected from:
    (1) hydroxy,
    (2) C$_1$–C$_5$-alkoxy,
    (3) C$_1$–C$_5$-alkoxycarbonyl,
    (4) C$_1$–C$_4$-alkylcarbonyloxy,
    (5) C$_3$–C$_8$-cycloalkyl,
    (6) phenyl, naphthyl or biphenyl,
    (7) substituted phenyl, naphthyl or biphenyl in which the substituents are V$_1$, V$_2$, V$_3$, V$_4$ and V$_5$,
    (8) C$_1$–C$_5$-alkyl-S(O)$_p$
    (9) phenyl-S(O)$_p$
    (10) substituted phenyl-S(O)$_p$ in which the substituent is V$_1$,
    (11) oxo,
    (12) carboxy,
    (13) C$_1$–C$_5$-alkylaminocarbonyl,
    (14) —NR$^{21}$COR$^{22}$,
    (15) —NR$^{21}$CO$_2$R$^{22}$,
    (16) —NR$^{21}$CONR$^{21}$R$^{22}$,
    (17) —OCONR$^{21}$R$^{22}$, or
    (18) —CN;
  (d) mono-, di-, tri-, or polyfluoro-C$_1$–C$_{10}$-alkyl,
  (e) C$_2$–C$_{10}$-alkenyl,
  (f) C$_2$–C$_{10}$-alkynyl,
  (g) C$_3$–C$_8$-cycloalkyl,
  (h) substituted C$_3$–C$_8$-cycloalkyl or substituted C$_3$–C$_8$-cycloalkyl-C$_1$–C$_4$-alkyl in which one or more substituent(s) is selected from:
    (1) hydroxy,
    (2) C$_1$–C$_5$-alkoxy,
    (3) C$_1$–C$_5$-alkoxycarbonyl,
    (4) C$_1$–C$_4$-alkylcarbonyloxy,
    (5) C$_1$–C$_6$-alkyl,
    (6) phenyl, naphthyl or biphenyl,
    (7) substituted phenyl, naphthyl or biphenyl in which the substituents are V$_1$, V$_2$, V$_3$, V$_4$ and V$_5$,
    (8) oxo,
    (9) carboxy,
    (10) C$_1$–C$_5$-alkylaminocarbonyl,
    (11) —NR$^{21}$COR$^{22}$,
    (12) —NR$^{21}$CO$_2$R$^{22}$,
    (13) —OCONR$^{21}$R$^{22}$, or
    (14) —CN;
  (i) phenyl, naphthyl or biphenyl,
  (j) substituted phenyl, naphthyl or biphenyl in which the substituents are V$_1$, V$_2$, V$_3$, V$_4$ and V$_5$,
  (k) phenyl-(CH$_2$)$_r$—(Q)$_c$—(CH$_2$)$_r$—,
  (l) substituted phenyl-(CH$_2$)$_r$—(Q)$_c$—(CH$_2$)$_r$—,
  (m) heterocycle-(CH$_2$)$_r$—(Q)$_c$—(CH$_2$)$_r$—, wherein the heterocycle is 5- or 6-membered containing one or two heteroatoms such as pyridine, furan, pyrrole, imidazole or thiazole and unsubstituted or substituted with V$_1$ and V$_2$;
V$_1$, V$_2$, V$_3$, V$_4$ and V$_5$ are independently selected from:
  (a) hydrogen,
  (b) C$_1$–C$_5$-alkoxy,
  (c) C$_1$–C$_5$-alkyl,
  (d) hydroxy,
  (e) NR$^9$R$^{10}$,
  (f) CO$_2$R$^9$,
  (g) trifluoromethyl,
  (h) Cl, Br, I, F,
  (i) hydroxy-C$_1$–C$_4$-alkyl,
  (j) -1H-tetrazol-5-yl,
  (k) —NH—SO$_2$CF$_3$,
  (l) CN,
  (m) NO$_2$,
  (n) C$_1$–C$_5$-alkyl-CO$_2$R$^9$,
  (o) aryl,
  (p) aryl-C$_1$–C$_3$-alkyl,
  (q) heteroaryl,
  (r) C$_1$–C$_5$-alkyl-CONR$^9$R$^{10}$,
  (s) —CONR$^9$R$^{10}$,
  (t) 2-oxazolin-2-yl optionally bearing one or more C$_1$–C$_4$-alkyl substituents, (u) C$_1$–C$_5$-alkyl-S(O)$_p$,
  (v) (CH$_2$)$_t$OCOR$^{22}$,
  (w) (CH$_2$)$_t$NR$^{21}$COR$^{22}$,
  (x) (CH$_2$)$_t$NR$^{21}$CO$_2$R$^{22}$,
  (y) (CH$_2$)$_t$NR$^{21}$CONR$^{21}$R$^{22}$, or
  (z) aryl-C$_1$–C$_3$-alkoxy;
u is 1; and
X is:
  (a) a single bond,
  (b) —C(O)—, or
  (c) —NR$^{15}$C(O)—.

In one class of this embodiment are those compounds of formula (I) wherein:
E is a single bond or —S—;
R$^1$ is:
R$^6$ is
  (a) C$_1$–C$_6$ alkyl unsubstituted or substituted with —F, —CF$_3$, cyclopropyl or C$_1$–C$_2$-alkylcyclopropyl; or (b) cyclopropyl, unsubstituted or substituted with —$CH_3$, —$C_2H_5$, —$CF_3$, or —$CF_2CF_3$;

A is =O, =S or =$NR^{21}$;

B is
(a) H provided A is not $NR^{21}$,
(b) $C_1$-$C_{10}$-alkyl,
(c) $C_3$-$C_8$-cycloalkyl,
(d) $C_3$-$C_8$-cycloalkyl-$C_1$-$C_4$-alkyl,
(e) substituted $C_1$-$C_{10}$-alkyl, $C_3$-$C_8$-cycloalkyl, or $C_3$-$C_8$-cycloalkyl-$C_1$-$C_4$-alkyl each of which can have one or two substituents selected from the group consisting of:
(1) hydroxy,
(2) $C_1$-$C_5$-alkoxy,
(3) $C_1$-$C_5$-alkoxycarbonyl,
(4) phenyl, naphthyl or biphenyl,
(5) substituted phenyl, naphthyl or biphenyl wherein the substituents are $V_1$, $V_2$, $V_3$, $V_4$, and $V_5$,
(6) carboxy,
(7) $C_1$-$C_5$-alkylaminocarbonyl,
(8) oxo,
(9) —$NR^{21}COR^{22}$,
(10) —$NR^{21}CO_2R^{22}$,
(11) —$OCONR^{21}R^{22}$, or
(12) —CN,
(f) mono-, di-, tri-, or polyfluoro-$C_1$-$C_{10}$-alkyl,
(g) phenyl, naphthyl or biphenyl,
(h) phenyl, naphthyl or biphenyl substituted with $V_1$, $V_2$, $V_3$, $V_4$ and $V_5$,
(i) phenyl—$(CH_2)_r$—$(Q)_c$—$(CH_2)_t$—,
(j) phenyl—$(CH_2)_r$—$(Q)_c$—$(CH_2)_t$— in which the phenyl is substituted with $V_1$, $V_2$, $V_3$, $V_4$ and $V_5$,

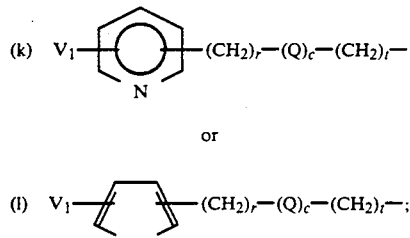

$V_1$, $V_2$, $V_3$, $V_4$ and $V_5$ are selected from:
(a) hydrogen,
(b) $C_1$-$C_5$-alkyl,
(c) $C_1$-$C_5$-alkoxy,
(d) $CO_2R^9$,
(e) Cl, Br, I, F,
(f) hydroxy-$C_1$-$C_4$-alkyl-,
(g) $C_1$-$C_5$-alkyl-$CO_2R^9$,
(h) $C_1$-$C_5$-alkyl-$CONR^9R^{10}$,
(i) $CONR^9R^{10}$,
(j) CN,
(k) $NO_2$,
(l) $CF_3$,
(m) aryl,
(n) heteroaryl,
(o) 2-oxazolin-2-yl optionally bearing one or more $C_1$-$C_4$-alkyl substituents,
(p) $C_1$-$C_5$-alkyl-$S(O)_p$,
(q) $(CH_2)_rOCOR^{22}$,
(r) $(CH_2)_rNR^{21}COR^{22}$,
(s) $(CH_2)_rNR^{21}CO_2R^{22}$,
(t) hydroxy,
(u) $NR^9R^{10}$,
(v) aryl-$C_1$-$C_3$-alkyl, or
(w) aryl-$C_1$-$C_3$-alkoxy.

A subclass of the foregoing class of compounds is that wherein:

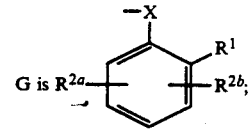

$R^{2a}$, $R^{2b}$, $R^{3a}$, and $R^{3b}$ are each H; and
X is a single bond.

Another subclass is that comprising those compounds of formula (I) wherein:
G is $R^1$;
$R^1$ is —$SO_2NHCOR^{23}$, —$SO_2NHCONR^{23}R^{24}$, —$SO_2NHCOOR^{23}$, —$SO_2NHOR^{24}$, —$CH_2SO_2NHCOR^{23}$, or -1H-tetrazol-5-yl;
$R^{3a}$ is H; and
$R^{3b}$ is H, F, Cl, $CF_3$, $CH_3$, $OCH_3$, or $NO_2$.

DISCUSSION OF CHEMISTRY AND REACTION SCHEMES

The compounds of Formula I can be prepared by a variety of methods typified by those described below. General synthetic methods for 2,4,5-trisubstituted-2,4-dihydro-3H-1,2,4-triazol-3-ones and -triazole-3-thiones are discussed in books or review articles such as:

(1) C. Temple and J. A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365–442.

(2) J. B. Polya, *Comprehensive Heterocyclic Chemistry. The Structure, Reactions, Synthesis and Uses of Heterocyclic Compounds*, A. R. Katritzky and C. W. Rees, eds., Vol. 5, Pergamon Press, Oxford, 1984, pp. 733–790.

(3) J. H. Boyer, *Heterocyclic Compounds*, R. C. Elderfield, ed., Vol. 7, John Wiley & Sons, New York, 1961, pp. 384–461.

In general, the compounds of Formula I are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate of isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "$ArCH_2$" substituent present at $N^4$ of the triazole derivatives or in their precursors is any substituted arylmethyl moiety consistent with the definition of the $N^4$ substituent in Formula I or which may be transformed to such a grouping either before or after the assembly of the triazole ring system. Such transformations may involve protection and/or deprotection, formation of the "X" linkage between the two aromatic rings as shown in Formula I, or other modifications. It is also to be understood that in most of the Reaction Schemes, the "ArCH$_2$" (Ar=aryl) substituent may be replaced by the homologous "Ar(CH$_2$)$_2$" group as consistent with the definition of Formula I.

It is further to be understood that in the generalized schemes below, unless specified otherwise, the R, R' and R" groups represent functionalized or unfunctionalized alkyl, aryl, heteroaryl, aralkyl, and the like, while Ar' represents a functionalized or unfunctionalized aryl or heteroaryl group. The moiety, R'X, represents an alkylating agent in which R' is typically a functionalized or unfunctionalized alkyl or aralkyl group, while X is a leaving group such as chloro, bromo, iodo, methanesulfonate, or p-toluenesulfonate. In structures showing an "X" group double-bonded to a carbon atom (as in 22 and products derived therefrom), X is O or S.

REACTION SCHEME 1

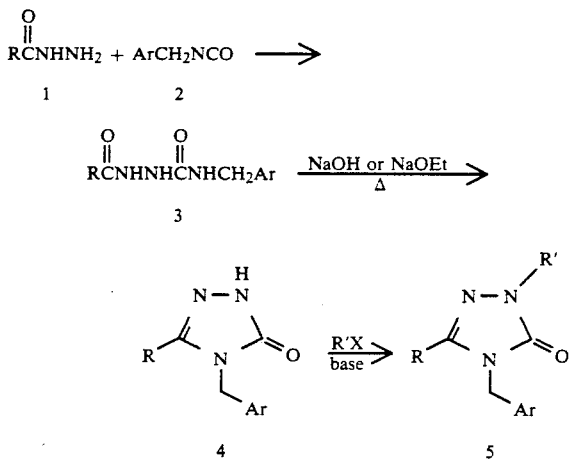

One of the most widely used routes to 2,4,5-trisubstituted-2,4-dihydro-3H-1,2,4-triazol-3-ones ("triazolinones") is shown in Reaction Scheme 1 in its adaptation for the synthesis of compounds of Formula I. Reaction of a carboxylic acid hydrazide 1 (readily obtained from the corresponding ester) with the appropriate arylmethyl isocyanate 2 gives the 1-acyl-4-(arylmethyl)-semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent R'X, where R' is alkyl, aralkyl, etc., and X is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J. P. Yevich, U.S. Pat. No. 4,613,600 (1986), and (in part) H. Gehlen and W. Schade, *Liebigs Ann. Chem.*, 675, 180 (1964), G. Palazzo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Beranek, *Collect. Czech. Chem. Commun.*, 50, 779 (1985).

REACTION SCHEME 2

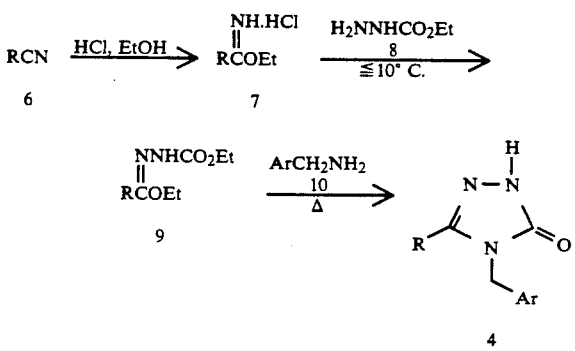

A highly useful alternative route to 4 is shown in Reaction Scheme 2. This approach has been described by M. Pesson, S. Dupin, and M. Antoine, *Compt. Rend.*, 253, 285 (1961) and R. Un and A. Ikizler, *Chim. Acta Turc.*, 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°–150° C.). As in Reaction Scheme 1, 4 can be alkylated to give the trisubstituted triazolinone 5.

REACTION SCHEME 3

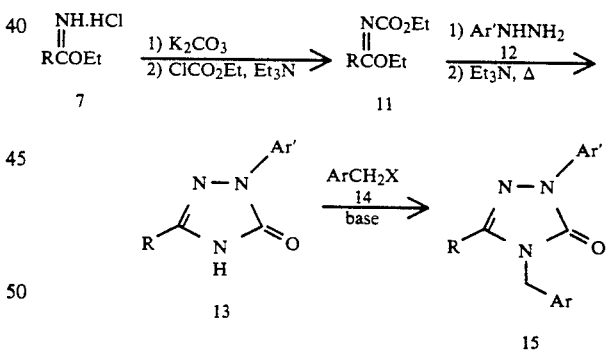

The procedures of Reaction Schemes 1 and 2 are not suitable for the introduction of most aryl or heteroaryl substituents at N$^2$. In contrast, the procedures of Reaction Schemes 3 to 6 are especially well suited for the synthesis of compounds of Formula I having aryl or heteroaryl substituents at N$^2$, since the triazolinone ring is constructed with the N$^2$-substituent in place, whereas the N$^4$-substituent is introduced subsequently by alkylation. Reaction Scheme 3 presents a route patterned after that reported by K. Yabutani, K. Taninaka, M. Kajioka, K. Takagi, H. Matsui, K. Sutoh, and M. Yamamoto, European Patent Application 220,952 (1987). The N-carbethoxy imidate 11 (obtained by reaction of 7 with ethyl chloroformate) is treated with an arylhydrazine 12 (or analog), typically at about 40°–50° C. Without isolation of the intermediate, further heating at elevated temperature (usually in the range of 90°-150° C.) in the presence of a tertiary amine such as triethylamine effects cyclization to the triazolinone 13. In the presence of a suitable base (e.g., sodium hydride, sodium alkoxide, sodium hydroxide) treatment of 13 with the appropriate ArCH$_2$X, where X=bromo, iodo, chloro, methanesulfonate, p-toluenesulfonate, and the like, yields the N$^4$-alkylated product 15. A variant of the method using a thioimidate has been described by M. Kajioka, H. Kurono, K. Okawa, and M. Harada, U.S. Pat. No. 4,318,731 (1982).

REACTION SCHEME 4

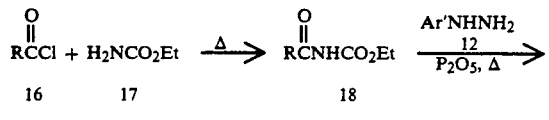

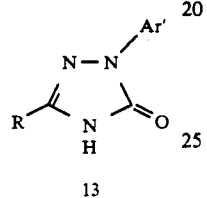

13

An alternative route to the N$^2$-substituted triazolinone intermediate 13 is shown in Reaction Scheme 4. This chemistry has been described by T. N. Ghosh and M. V. Betrabet, *J. Indian Chem. Soc.*, 7, 899 (1930), S. Bellioni, *Ann. Chim. (Rome)*, 52, 187 (1962), G. Palazzo and G. Picconi, *Boll. Chim. Farm.*, 105, 217 (1966), and British Patent 1,021,070 (1966). An acid chloride 16 is heated with urethane (17) (typically at 80°-100° C.), to give the acylurethane 18. Reaction of 18 with an arylhydrazine 12 and phosphorus pentoxide (usually in toluene or xylene at reflux) gives 13, which can then be further alkylated on N$^4$ as in Reaction Scheme 3. A (thioacyl)urethane modification of this pathway has been reported by D. L. Temple, Jr., and W. G. Lobeck, Jr., U.S. Pat. No. 4,487,773 (1984).

REACTION SCHEME 5

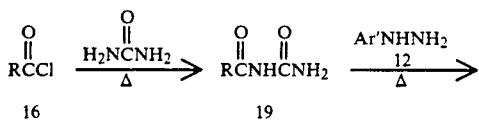

-continued
REACTION SCHEME 5

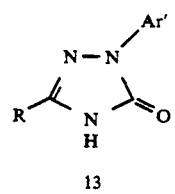

13

A variation of Reaction Scheme 4, shown in Reaction Scheme 5, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°-200° C.) is converted to the triazolinone intermediate 13.

REACTION SCHEME 6

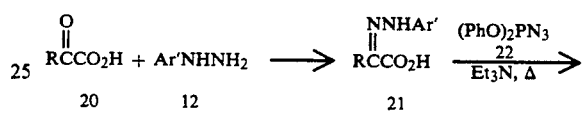

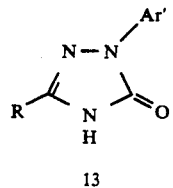

13

In a quite different approach (Reaction Scheme 6), L. Maravetz, U.S. Pat. No. 4,705,557 (1987) and G. Theodoridis, International Patent Application WO87/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°-115° C.). In the last step, an intermediate acyl azide loses nitrogen and undergoes the Curtius rearrangement to an isocyanate, which undergoes ring closure. As shown in Reaction Scheme 3, 13 can then be alkylated on N$^4$ to give the trisubstituted triazolinone 15.

REACTION SCHEME 7

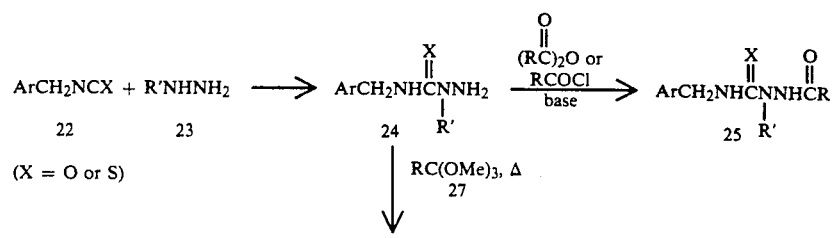

REACTION SCHEME 7 -continued

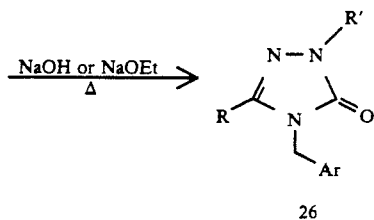

2,4,5-Trisubstituted-2,4-dihydro-3H-1,2,4-triazole-3-thiones ("triazolinethiones") cannot generally be prepared by routes analogous to those in Reaction Schemes 1 to 6 because of the propensity for alkylation to occur on sulfur rather than on the open ring nitrogen. It is thus preferable to have all of the substitutents in place at the time of the ring closure to form the heterocycle. As shown in Reaction Scheme 7, for certain R' groups (e.g., R'=CH$_3$), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

REACTION SCHEME 8

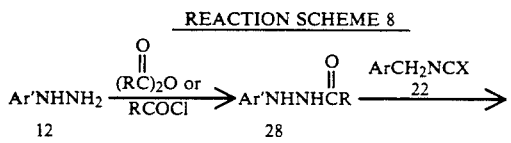

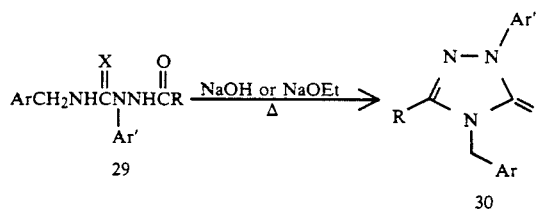

In Reaction Scheme 8, acylation of an aryl-or heteroaryl hydrazine gives 28, which can be reacted with the isocyanate or isothiocyanate 22 to yield the 1-acyl-2,4-disubstituted-semicarbazide or -thiosemicarbazide 29. Cyclization of 29 upon heating with hydroxide or alkoxide affords the triazolinone or triazolinethione 30. This chemistry has been described by H. Gehlen and W. Schade, *Liebigs Ann. Chem.*, 675, 180 (1964).

REACTION SCHEME 9

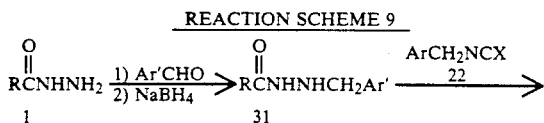

REACTION SCHEME 9 -continued

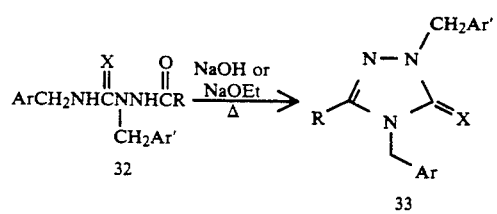

The method of F. Russo, M. Santagati, and G. Pappalardo [*Ann. Chim. (Rome)*, 62, 351 (1972)] (Reaction Scheme 9) is useful for the synthesis of trisubstituted triazolinones and triazolinethiones having benzylic substituents at N$^2$. Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

REACTION SCHEME 10

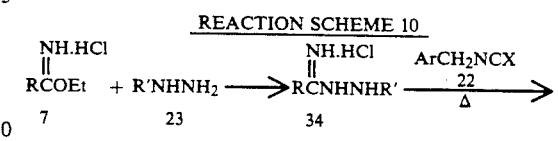

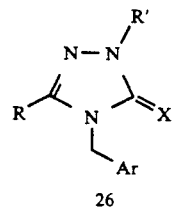

In another approach (Reaction Scheme 10), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.*, 37, 293 (1980); T. Bany, *Rocz. Chem.*, 42, 247 (1968); and, T. Bany and M. Dobosz, *Ann. Univ. Mariae Curie-Sklodowska, Sect. AA,* 26/27, 23 (1971).

REACTION SCHEME 11

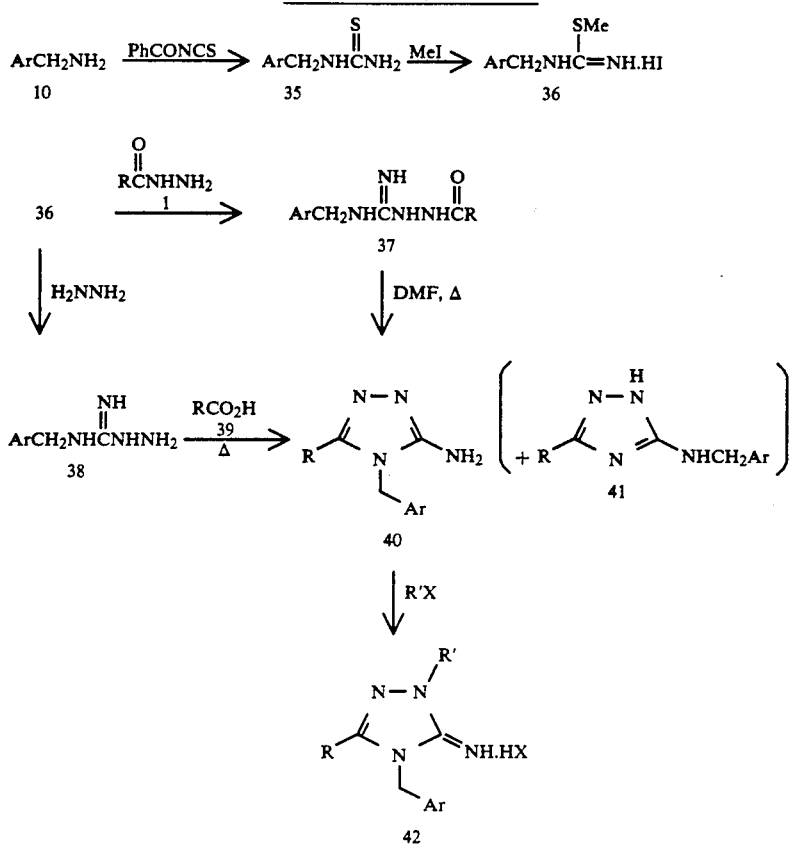

A route to 2,4,5-trisubstituted-2,4-dihydro-3H-1,2,4-triazol-3-imines ("triazolinimines") is outlined in Reaction Scheme 11. Reaction of the (arylmethyl)amine 10 with benzoyl isothiocyanate (or by other means) gives the substituted thiourea 35, which is methylated to prepare the isothiourea derivative 36. Compound 36 can be transformed to the acylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate R'X (where X is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

REACTION SCHEME 12

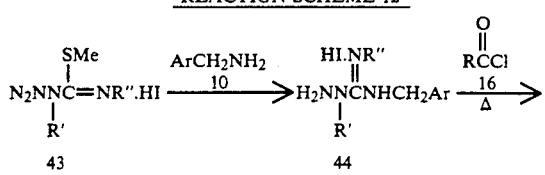

-continued
REACTION SCHEME 12

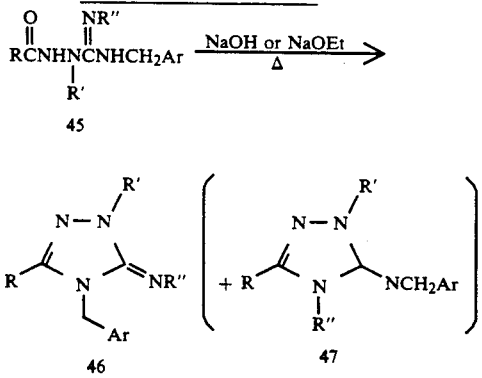

The route shown in Reaction Scheme 12 utilizes chemistry reported by E. Akerblom, *Acta Chem. Scand.*, 19, 1135 (1965). The substituted isothiourea 43 is treated with amine 10 to give the aminoguanidine derivative 44. Acylation of 44 with the acid chloride 16 provides the intermediate 45, which can be cyclized by heating with hydroxide or alkoxide. The desired triazolinimine 46 is separated from the isomeric product 47.

REACTION SCHEME 13

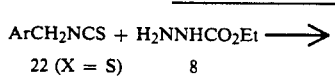

-continued
REACTION SCHEME 13

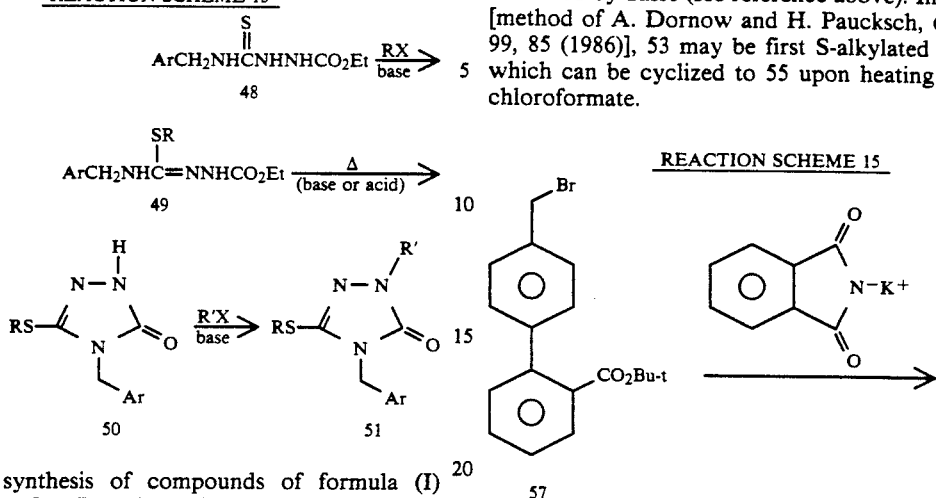

For the synthesis of compounds of formula (I) wherein E=—S—, Reaction Schemes 13 and 14 may be utilized. In Reaction Scheme 13, the isothiocyanate 22 is reacted with ethyl carbazate (8) to give the 1-(carbethoxy)thiosemicarbazide 48. By standard conditions, 48 is S-alkylated to yield 49, which can be cyclized to the triazolinone 50 by heating, optionally in the presence of base or acid [F. Kurzer and D. R. Hanks, *Chem. Ind. (London)*, 1143 (1966)]. Finally, alkylation of the triazolinone as in Reaction Scheme 1 provides the fully substituted product 51.

REACTION SCHEME 14

Following the chemistry of K. Sasse [*Liebigs Ann. Chem.*, 735, 158 (1970)](Reaction Scheme 14), an arylhydrazine 12 is treated with carbon disulfide in the presence of base followed by treatment with methyl iodide to give the dithiocarbamoyl derivative 52. Reaction of 52 with the (arylmethyl)amine 10 yields the 1,4-disubstituted thiosemicarbazide 53. Cyclization of 53 to 54 is accomplished in two steps by first heating with diethyl carbonate and then treating with hydroxide to induce ring closure. Further treatment of 54 with an alkyl halide gives the desired S-alkyl triazolinone 55. A modification allowing the synthesis of compounds analogous to 55 in which the "Ar" substituent is replaced by an alkyl (or aralkyl) group has also been described by Sasse (see reference above). In a variation [method of A. Dornow and H. Paucksch, *Chem. Ber.*, 99, 85 (1986)], 53 may be first S-alkylated to give 56, which can be cyclized to 55 upon heating with ethyl chloroformate.

REACTION SCHEME 15

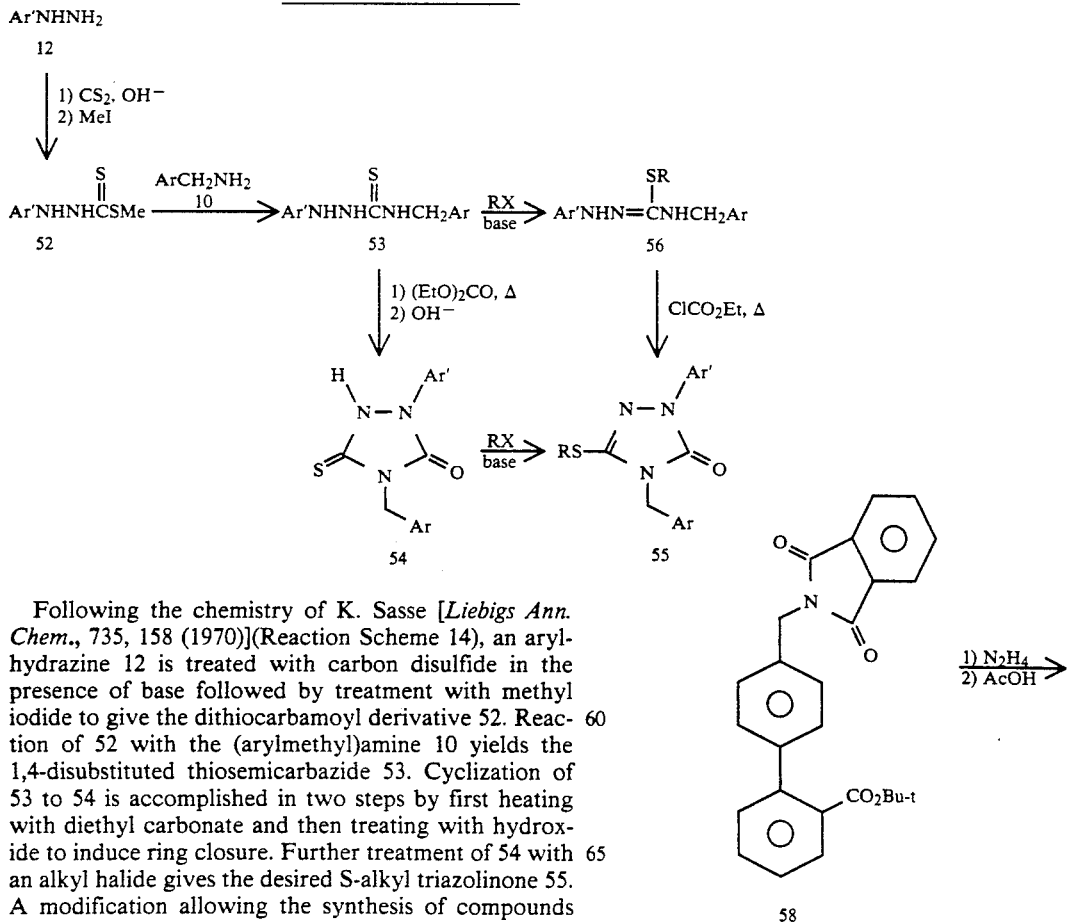

-continued
REACTION SCHEME 15

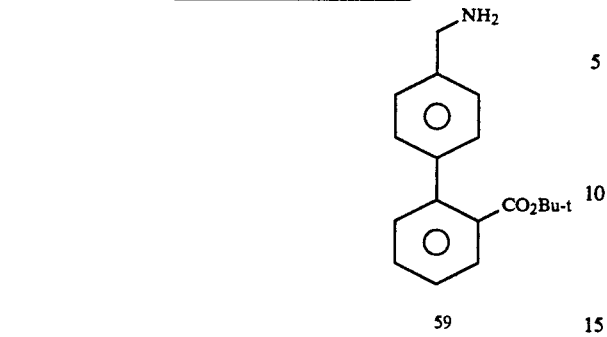

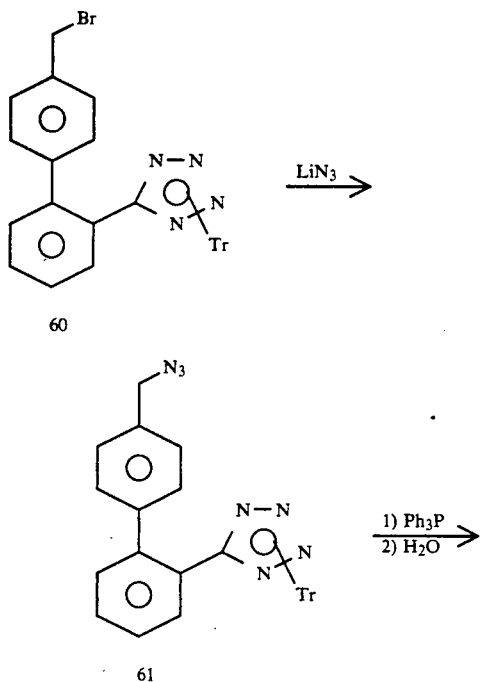

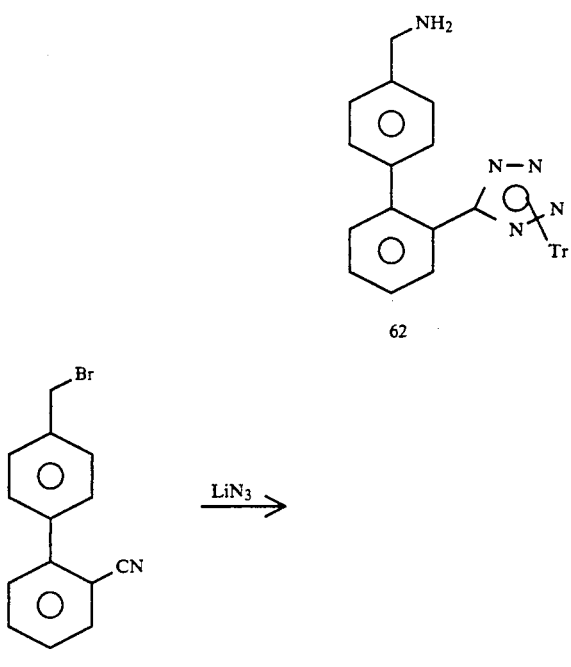

-continued
REACTION SCHEME 15

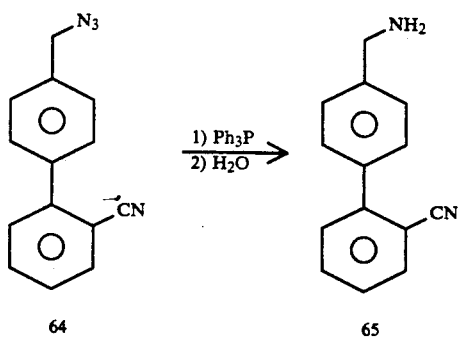

Reaction Scheme 15 shows routes to key intermediates used for incorporation of a (2'-carboxybiphenyl-4-yl)methyl or [2'-(5-tetrazolyl)biphenyl-4-yl]methyl substituent into a 2,4-dihydro-3H-1,2,4-triazol-3-one or -triazole-3-thione at the 4-position. One starting material, 4-bromomethyl-2'-(t-butoxycarbonyl)biphenyl (57), can be prepared as described in European Patent Application 253,310 (or as modified in U.S. application Ser. No. 351,508 filed May 15, 1989. Treatment of 57 with potassium phthalimide at room temperature in a suitable solvent such as N,N-dimethylformamide gives the phthalimido product 58, which is converted to the amine 59 by a standard hydrazinolysis procedure. Alternatively, using the methods described in European Patent Application 253,310, 57 may be treated with sodium azide in dimethylformamide, and the resulting azide intermediate may be reduced to the amine 59 by hydrogenation in the presence of palladium catalyst or by other methods known in the literature. After conversion of 57 or 59 to a triazolinone, triazolinethione, or triazolinimine by methods illustrated in the previous schemes, the t-butyl ester is readily deprotected by treatment with trifluoroacetic acid at room temperature.

Transformation of 5-[4'-(bromomethyl)biphenyl-2-yl]-N-trityltetrazole (60) (prepared as in European Patent Application 291,969 or as modified in U.S. application Ser. No. 351,508 filed May 15, 1989 to the azido intermediate 61 is accomplished by standard means such as treatment with lithium azide in dimethyl sulfoxide at room temperature. Reduction of 61 to the amine 62 proceeds readily using the conditions of M. Vaultier, N. Knouzi, and R. Carrie [*Tetrahedron Lett.*, 24, 763 (1983)] (triphenylphosphine in tetrahydrofuran followed by water). By use of the methods outlined in previous schemes, 60 or 62 can be converted to a triazolinone, triazolinethione, or triazolinimine. Removal of the trityl protecting group from the tetrazole is achieved by warming in aqueous acetic acid.

Alternatively, 4-bromomethyl-2'-cyanobiphenyl (63) (described in European Patent Application 253,310) can be converted to the azide intermediate 64 as disclosed in U.S. patent application Ser. No. filed, submitted for filing Jul. 17, 1989). Reduction of 64 by the method described above for the synthesis of 62 gives the amine 65. After conversion of 63 or 65 to a triazolinone, triazolinethione, or triazolinimine by methods illustrated in the previous schemes, the cyano substituent may be converted to the desired 5-tetrazolyl group by reaction with trimethyltin azide at elevated temperature in a suitable solvent such as toluene or xylene according to methods described in European Patent Application 291,969. Final destannylation to the free tetrazole may be accomplished by treatment with silica gel as described in U.S. patent application Ser. No. 382,138 filed Jul. 19, 1989.

Although specific examples have been shown for the synthesis of compounds of formula (I) wherein X is a single bond, these methods are readily extended to the preparation of compounds of formula (I) having other X linkages allowed by the specifications. Depending on the nature of X, this linkage may be constructed either before or after assembly of the triazole ring. The construction of heterocyclic side chains analogous to the $N^4$ side chain of compounds of formula (I), in which variations of the X group are exemplified, has been disclosed in U.S. patent application Ser. No. 351,508, filed May 15, 1989, U.S. patent application Ser. No. 382,138, filed Jul. 19, 1989 and European Patent Application 253,310.

REACTION SCHEME 16

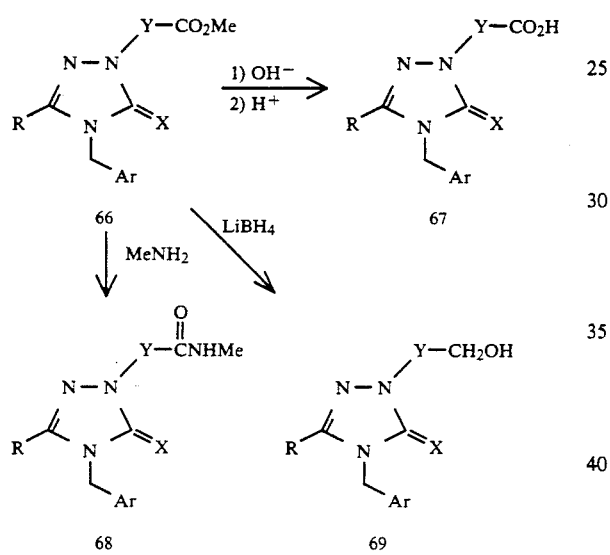

wherein:

Y represents an alkyl, aryl, heteroaryl, or aralkyl group bearing the designated substituent (i.e., carbomethoxy, carboxy, etc.)

Further transformations of substituent functional groups can be carried out after assembly of the triazole ring and either before or after full elaboration of the arylmethyl substituent at $N^4$. Typical examples are shown in Reaction Scheme 16. Thus the methyl ester of 66 can be saponified by treatment with aqueous sodium hydroxide (optionally in the presence of a cosolvent such as alcohol, tetrahydrofuran, or dioxane) at room temperature to give, after acidification, the acid 67. The N-methyl amide 68 is readily obtained by reaction of 66 with excess aqueous methylamine at room temperature in the presence of a cosolvent such as methanol. Reduction of the methyl ester 66 to the alcohol 69 can be accomplished by treatment with lithium borohydride in a solvent such as tetrahydrofuran. These examples are in no way exclusive of other functional group transformations which can be accomplished after formation of the triazolinone, triazolinethione, or triazolinimine system, and which will be apparent to anyone skilled in the art.

REACTION SCHEME 17

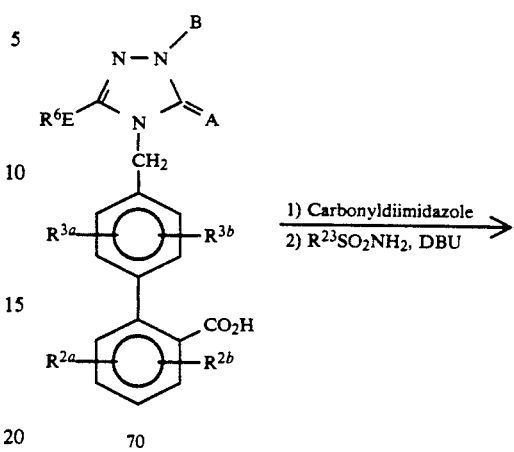

Alternative Methods:

a) (i) $SOCl_2$, $\Delta$ (ii) $R^{23}SO_2NH-M^{30}$ (where M is Na or Li)

b) (i) $(COCl)_2$/DMF, $-20°$ C. (ii) $R^{23}SO_2NH-M^+$ c) (i) N-(N,N-Diphenylcarbamoyl)pyridinium chloride-/aq. NaOH (ii) $R^{23}SO_2NH-M^+$.

Compounds of formula (I) wherein $R^1$ is —CONHSO$_2R^{23}$ (where $R^{23}$ is substituted or unsubstituted alkyl, aryl, or heteroaryl) may be prepared from the corresponding carboxylic acid derivatives (70) as outlined in Reaction Scheme 17. The carboxylic acid 70, obtained as described in Reaction Scheme 15 and preceding schemes (followed by deprotection of the t-butyl ester with trifluoroacetic acid), can be converted into the corresponding acid chloride by treatment with thionyl chloride at reflux or, preferably, with oxalyl chloride and a catalytic amount of dimethylformamide at low temperature [A. W. Burgstahler, et al., Synthesis, 767 (1976)]. The acid chloride can then be treated with the alkali metal salt of $R^{23}SO_2NH_2$ to form the desired acylsulfonamide 71. Alternatively, 71 may be prepared from 70 using N,N-diphenylcarbamoyl anhydride intermediates [F. J. Brown, et al., European Patent Application EP 199,543; K. L. Shepard and W. Halczenko, J. Heterocycl. Chem., 16, 321 (1979)]. Preferably, the carboxylic acid 70 is treated with carbonyldiimidazole to give an acyl-imidazole intermediate, which can then be treated with an appropriate aryl- or alkylsulfonamide in the presence of 1,8-diazabicyclo[5.4.0]undec-7-ene (DBU) to give the desired acylsulfonamide 71.
SCHEME 18
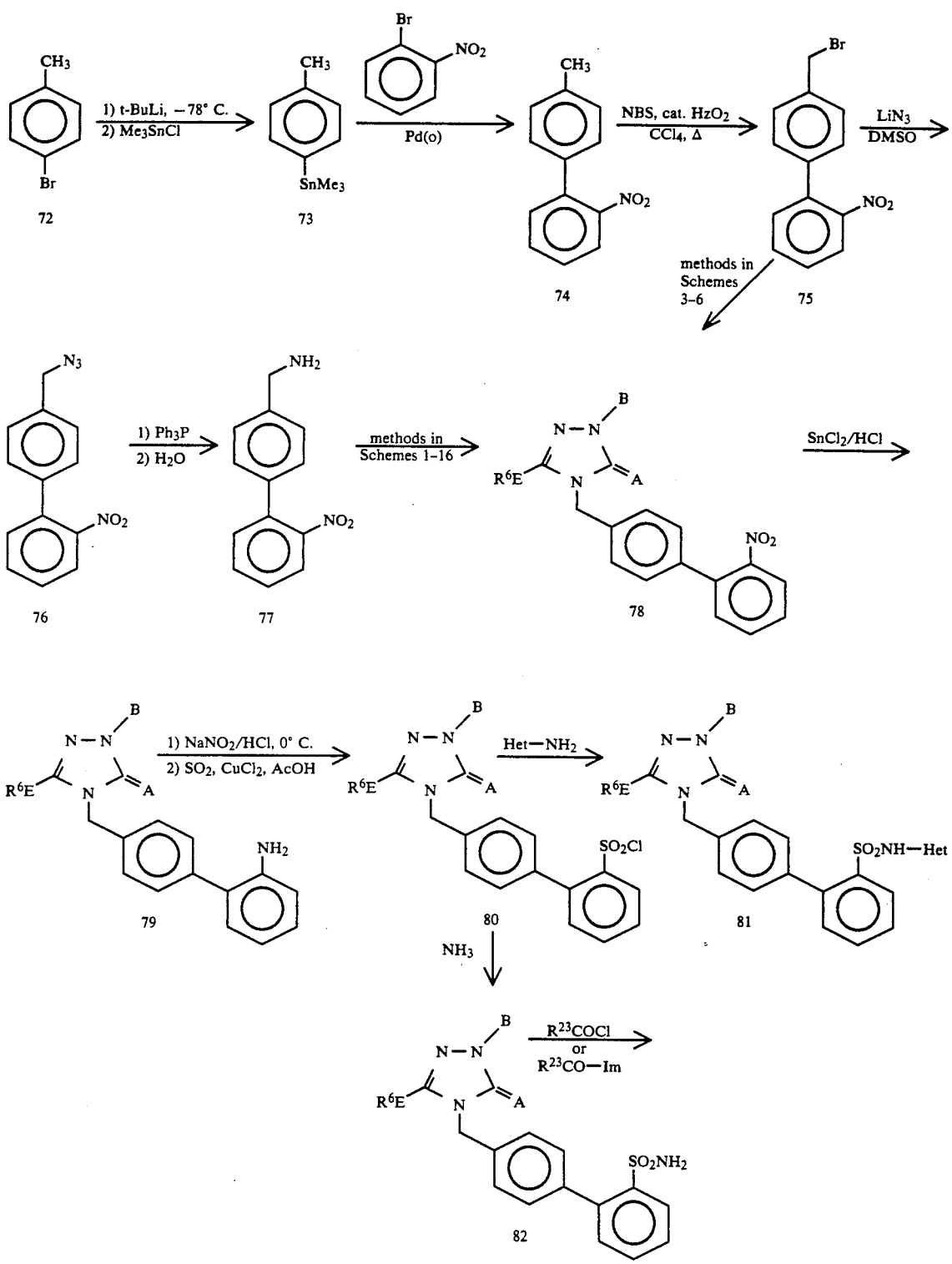

-continued
SCHEME 18

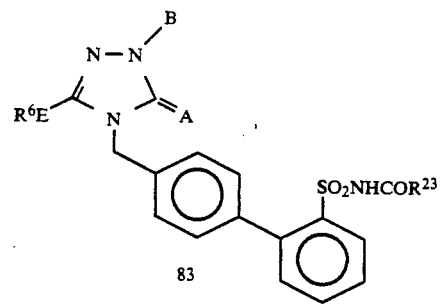

where
NBS = N-bromosuccinimide
Bz = benzoyl
Het = heteroaryl
Im = 1-imidazolyl.

The preparation of compounds of formula (I) wherein $R^1$ is —SO$_2$NH-heteroaryl or —SO$_2$NH-COR$^{23}$ is outlined in Reaction Scheme 18. p-Bromotoluene (72) is converted to the trimethylstannane derivative 73 [S. M. Moerlein, *J. Organometal. Chem.*, 319, 29 (1987)], which may be coupled with o-bromonitrobenzene in the presence of (Ph$_3$P)$_4$Pd or (Ph$_3$P)$_2$PdCl$_2$ catalyst to give the biphenyl derivative 74. Such couplings have been described by J. K. Stille, *Pure Appl. Chem.*, 57, 1771 (1985); T. R. Bailey, *Tetrahedron Lett.*, 27, 4407 (1986); and D. A. Widdowson and Y-Z. Zhang, *Tetrahedron*, 42, 2111 (1986). Bromination of 74 with N-bromosuccinimide in the presence of catalytic benzoyl peroxide gives 75, which upon treatment with lithium azide in DMSO yields the azido derivative 76. Reduction of 76 to the amine 77 may be accomplished by treatment with triphenylphosphine followed by water. In an alternative route, the bromo group of 75 may be displaced by potassium phthalimide. Hydrazinolysis of the phthalimide derivative yields 77.

By the methods described in the previous schemes, the amine 77 can be converted to a variety of triazolinones, triazolinethiones, and triazolinimines of the general formula 78. Certain triazolinones, especially those in which B is aryl or heteroaryl, may be made directly from 75 by alkylation of a pre-formed triazolinone as in Reaction Schemes 3-6. Reduction of the nitro group of 78, preferably with stannous chloride/hydrochloric acid gives the amino derivative 79. Diazotization of the amine 79 and reaction of the diazonium salt with sulfur dioxide in the presence of cupric chloride affords the corresponding arylsulfonyl chloride 80 [see H. Meerwein, et al., *Chem. Ber.*, 90, 841 (1957); A. J. Prinsen and H. Cerfontain, *Rec. Trav. Chim.*, 84, 24 (1965); E. E. Gilbert, *Synthesis*, 3 (1969); and references cited therein]. Treatment of the sulfonyl chloride 80 with an appropriate heteroaryl amine provides the N-heteroaryl sulfonamide 81. Reaction of the sulfonyl chloride with ammonia yields the sulfonamide 82, which is then treated with an appropriate acylating agent (such as an acid chloride, a carbamoyl chloride, or an acylimidazole derivative) to give the acylsulfonamide product 83.

SCHEME 19

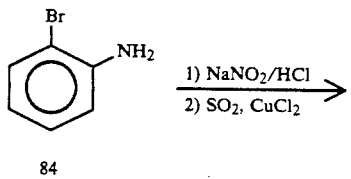

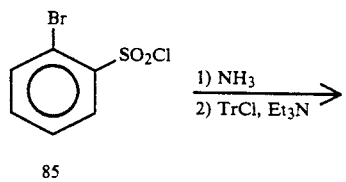

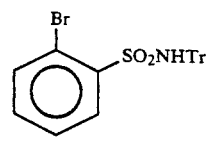

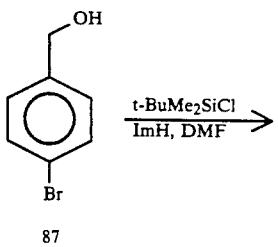

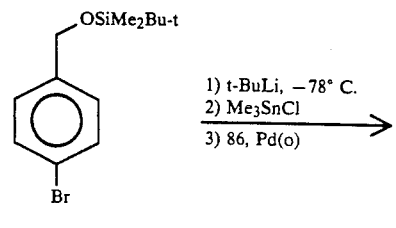

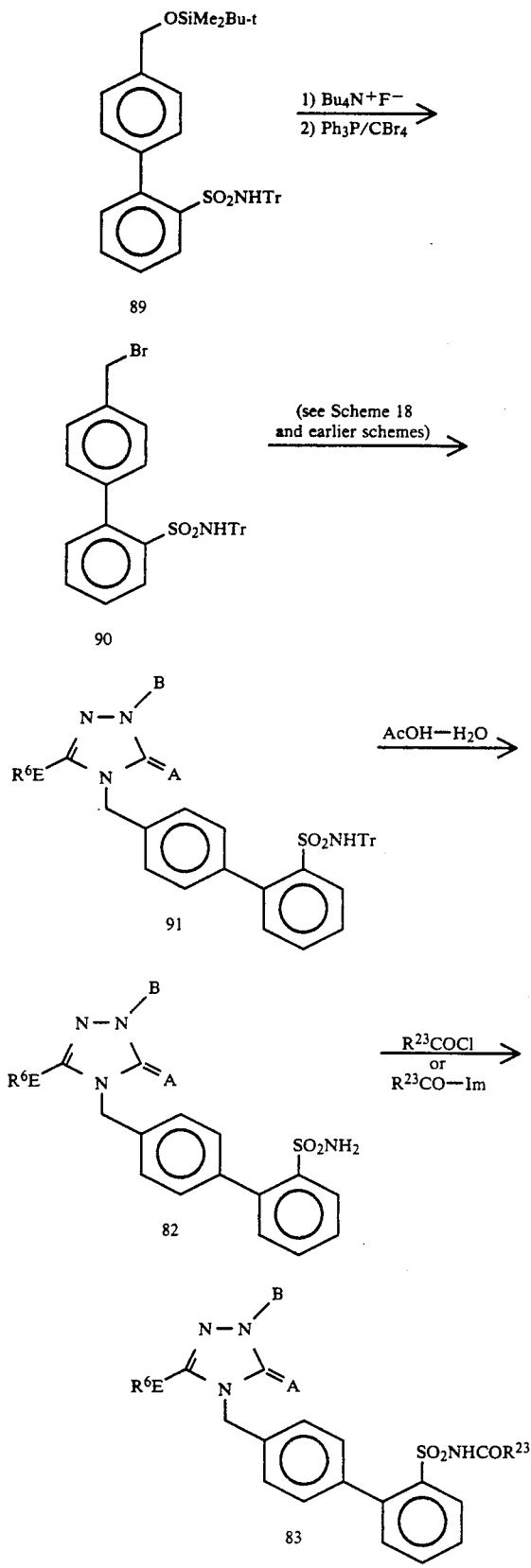

Tr=trityl (i.e., triphenylmethyl)
Im=1-imidazolyl.

Reaction Scheme 19 shows an alternative sequence leading to 83 in which a protected sulfonamide is present at the time of the biaryl coupling. By the methods described above, o-bromoaniline (84) is converted to the corresponding sulfonyl chloride 85. Treatment of 85 with ammonia and then with trityl chloride in the presence of triethylamine yields the N-trityl sulfonamide 86. p-Bromobenzyl alcohol (87) is t-butyldimethylsilylated, and the resulting 88 is coupled with 86 under the conditions described above to give the biphenyl product 89. The silyl group is removed with tetrabutylammonium fluoride, and treatment of the alcohol with triphenylphosphine/carbon tetrabromide gives the bromo derivative 90. Using the methods of Scheme 18 and earlier schemes, 90 may be transformed into a variety of triazoles of the general formula 91. The trityl protecting group is removed with aqueous acetic acid to give the free sulfonamide 82 which is acylated to yield the target 83 as in Scheme 18.

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Neurotensin is a peptide hormone and the assays described below have been developed to identify neurotensin antagonists and to determine their efficacy in vitro. The following three assays have been employed for that purpose.

Rat Forebrain Receptor Assay

Male rats are sacrificed by decapitation following ether anesthetization. Forebrains are homogenized using a polytron in 20 volumes 50 mM Tris HCl, pH 7.4, and centrifuged at 50,000×g for 20 min. The final pellet is resuspended at a concentration of 8 mg tissue (wet weight) per 0.750 ml of 50 mM Tris HCl, pH 7.4, which also contains 1 mM EDTA, 4 μg/ml bacitracin, 5 μM levocabastine HCl, 1 mM phenanthroline, 10 μg/ml soybean trypsin inhibitor and 100 μM phenyl methyl sulfonly fluoride. Assay tubes (13×100 polypropylene) receive 1) 100 μl buffer or 10 μM neurotensin (for non-specific binding) 2) 100 μl of 60 pM [$^{125}$I]neurotensin 3) 20 μl test compounds 4) 750 μl tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on as Packard Multu-Prias gamma counter.

Human HT-29 Cell Membrane Assay

HT-29 cells were routinely grown in 225 cm² Costar tissue culture flasks at 37° C. in a humidified atmosphere of 5% CO$_2$/95% air in Dulbecco's modified Eagle's medium with high glucose containing 50 U/ml penicillin, 50 μg/ml streptomycin, 5% fetal bovine serum and 5% newborn calf serum. Cells were subcultured with 0.25% trypsin at a ratio of 1:6 with confluence being reached at 48 to 72 hrs. Cells from confluent flasks (approx. 1×10$^8$ cells/flask) were harvested by scraping. The cells were pelleted by centrifugation (1000×g, 5 min), resuspended in 50 mM Tris HCl, pH 7.4, and homogenized with a polytron (setting 7 for 10 sec.). Cell membranes were washed twice by centrifugation (50,000×g, 15 min) and rehomogenization. The resulting pellet was either frozen at −70° C. for future use or run directly in the assay by resuspending at a concentration of 0.5×10$^6$ cells per 0.750 ml of assay buffer (50 mM Tris HCl, pH 7.4, containing 1 mM EDTA, 40 μg/ml bacitracin, 1 mM phenanthroline, 10 μg/ml soybean trypsin inhibitor and 100 μM phenylmethylsulfonyl fluoride).

Assay tubes (13×100 polypropylene) receive 1) 100 μl buffer or 10 μM neurotensin (for non-specific binding) 2) 100 μl of 60 pM [$^{125}$I]neurotensin 3) 20 μl test compounds 4) 750 μl cell membrane suspension an 5) enough buffer to bring final volume to 1 ml. After 30 minutes at room temperature, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on as Packard Multi-Prias gamma counter. [The above assay is derived from the assay described in Kitabgi, P. et al., Molecular Pharmacology, 18, 11-19 (1980)].

Neurotensin Binding Assay Using Human Frontal Cortex

Post-mortem human brain is obtained through the National Disease Research Interchange (Philadelphia, Pa.). The donors were without psychiatric or neurological abnormalities. Frontal cortex is dissected free of white matter and homogenized using a polytron in 20 volumes 50 mM Tris HCl, pH 7.4, and centrifuged at 50,000×g for 20 min. The resulting pellet is washed twice by rehomogenization and centrifugation as before. The final pellet is resuspended at a concentration of 8 mg tissue (wet weight) per 0.750 ml of 50 mM Tris HCl, pH 7.4, which also contains 1 mM EDTA, 4 μg/ml bacitracin, 1 mM phenanthroline, 10 μg/ml soybean trypsin inhibitor and 100 μM phenyl methyl sulfonly fluoride. Assay tubes (13×100 polypropylene) receive 1) 100 μl buffer or 10 μM neurotensin (for non-specific binding) 2) 100 μl of 60 pM [$^{125}$I]neurotensin 3) 20 μl test compounds 4) 750 μl tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on a Packard Multu-Prias gamma counter.

Using the methodology described above, representative compounds of the invention were evaluated and all were found to exhibit an activity of at least IC$_{50}$<50 μM thereby demonstrating and confirming the utility of the compounds of the invention as effective neurotensin antagonists.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds listed below are representative of the compounds of the invention and are prepared according to the procedures described in EP 412,594 published on Feb. 13, 1991:

5-n-Butyl-2,4-dihydro-4-[[2'-(5-tetrazolyl)biphenyl-4-yl]methyl]-3H-1,2,4-triazol-3-one 2-Benzyl-5-n-butyl-2,4-dihydro-4-[[2'-(5-tetrazolyl)-biphenyl-4-yl]methyl]-3H-1,2,4-triazol-3-one 5-n-Butyl-2,4-dihydro-2-phenyl-4-[[0 2'-(5-tetrazolyl)-biphenyl-4-yl]methyl-3H-1,2,4-triazol-3-one 5-n-Butyl-2-(2-chlorophenyl)-2,4-dihydro-4-[[2'-(5-tetrazolyl)biphenyl-4-yl]methyl-9 -3H-1,2,4-triazol-3-one 5-n-Butyl-2-[2-(carbomethoxy)benzyl]-2,4-dihydro-4-[[2'-(5-tetrazolyl)biphenyl-4-yl]methyl]-3H-1,2,4-triazol-3-one 5-n-Butyl-2-(2-carboxybenzyl)-2,4-dihydro-4-[[2'-(5-tetrazolyl)biphenyl-4-yl]methyl]-3H-1,2,4-triazol-3-one 5-n-Butyl-2,4-dihydro-2-[2-(hydroxymethyl)phenyl]-4-[[2'-(5-tetrazolyl)biphenyl-4-yl]methyl]-3H-1,2,4-triazol-3-one 2-[2-(Acetoxymethyl)phenyl]-5-n-butyl-2,4-dihydro-4-[[2'-(5-tetrazolyl)biphenyl-4-yl]-methyl]-3H-1,2,4-triazol-3-one 5-n-Butyl-2,4-dihydro-2-[4-methylbenzyl]-4-[[2'-(5-tetrazolyl)biphenyl-4-yl]methyl]-3H-1,2,4-triazol-3-one

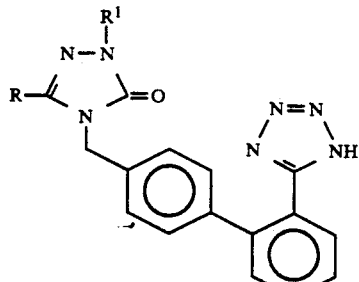

| | R | R¹ |
|---|---|---|
| (1) | n-Bu | s-Bu |
| (2) | n-Bu | 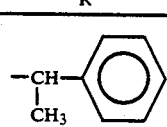 |
| (3) | n-Bu | 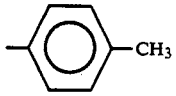 |
| (4) | n-Bu | 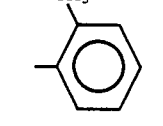 |
| (5) | n-Bu | 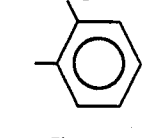 |
| (6) | n-Bu | 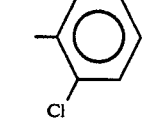 |

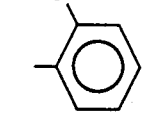

| | R | R¹ |
|---|---|---|
| (7) | n-Bu | 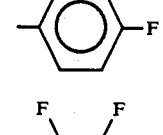 |
| (8) | n-Bu | |
| (9) | n-Bu | |
| (10) | n-Bu | |
| (11) | n-Bu | |
| (12) | n-Bu | |
| (13) | n-Bu | |
| (14) | n-Bu | 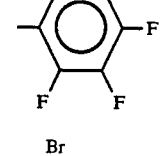 |
| (15) | n-Bu | 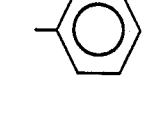 |

-continued
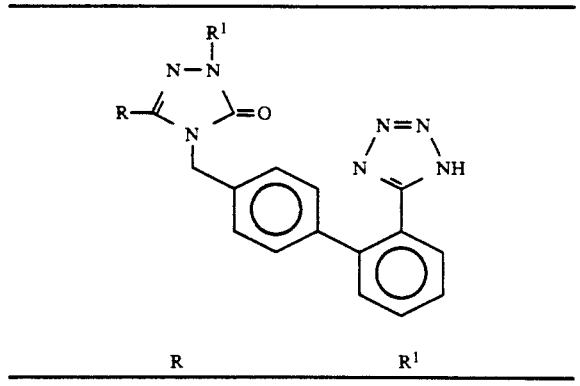
| | R | R¹ |
|---|---|---|
| (16) | n-Bu | 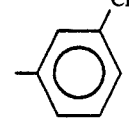 |
| (17) | n-Bu | 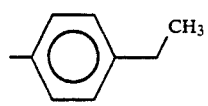 |
| (18) | n-Bu | 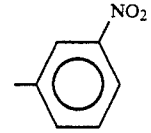 |
| (19) | n-Bu | 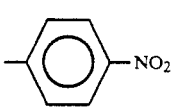 |
| (20) | n-Bu | 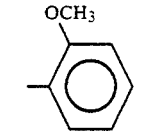 |
| (21) | n-Bu | 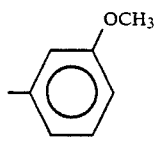 |
| (22) | n-Bu | 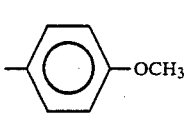 |
| (23) | n-Bu | 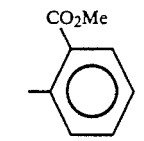 |
| (24) | n-Bu | 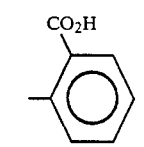 |
-continued
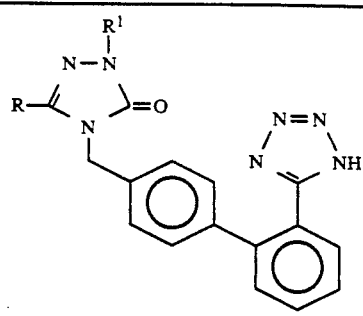
| | R | R¹ |
|---|---|---|
| (25) | n-Bu | 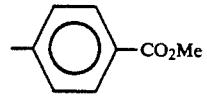 |
| (26) | n-Bu | 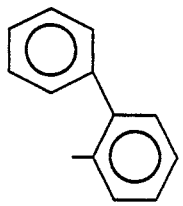 |
| (27) | n-Bu | 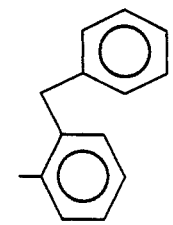 |
| (28) | n-Bu | 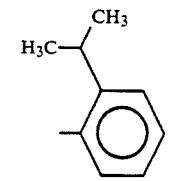 |
| (29) | n-Bu | 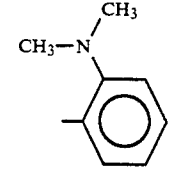 |
| (30) | n-Bu | 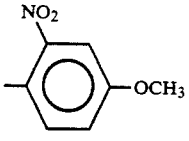 |
| (31) | n-Pr | 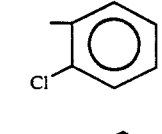 |
| (32) | n-Pr | 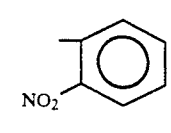 |

-continued

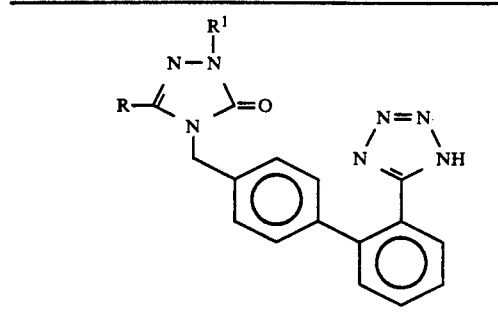

| | R | R¹ |
|---|---|---|
| (33) | n-C₅H₁₁ | 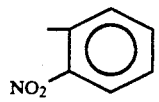 |
| (34) | n-Bu | 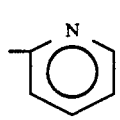 |
| (35) | n-Bu | —CH₂C₆F₅ |
| (36) | n-Bu | 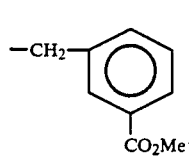 |
| (37) | n-Bu | 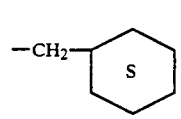 |
| (38) | n-Bu | —CH₃ |
| (39) | n-Bu | —CH₂CH₃ |
| (40) | n-Bu | —CH₂CH₂CH₃ |
| (41) | n-Bu | —CH(CH₃)₂ |
| (42) | n-Bu | —(CH₂)₃CH₃ |
| (43) | n-Bu | —CH₂CH(CH₃)₂ |
| (44) | n-Bu | 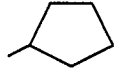 |
| (45) | n-Bu | —CH₂CO₂Me |
| (46) | n-Bu | —CH₂CF₃ |
| (47) | n-Pentyl | 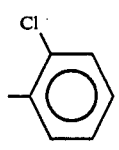 |
| (48) | n-Bu | 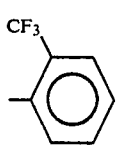 |
| (49) | n-Bu | —(CH₂)₂C₆H₅ |
| (50) | n-Bu | —CH(CH₃)CO₂Me |
| (51) | n-Bu | —CH(CH₃)CO₂H |

-continued

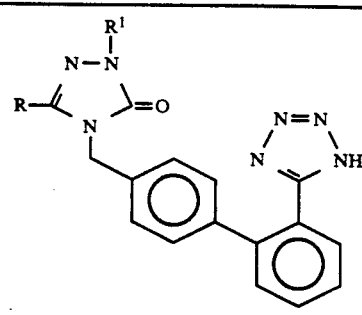

| | R | R¹ |
|---|---|---|
| (52) | n-Bu | 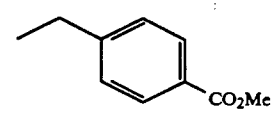 |
| (53) | n-Bu | 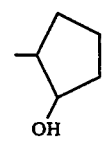 |
| (54) | n-Bu | —CH₂C(CH₃)₃ |
| (55) | n-Bu | -t-Bu |
| (56) | n-Bu | —(CH₂)₃C₆H₅ |
| (57) | n-Bu | 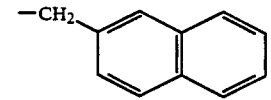 |
| (58) | n-Bu | —CH(CH₃)CH₂OH |
| (59) | n-Bu | —CH₂◁ |
| (60) | 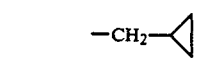 | —(CH₂)₂C₆H₅ |
| (61) |  | —(CH₂)₂C₆H₅ |
| (62) | 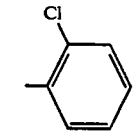 | 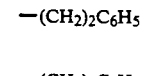 |

2-[3-(N-Benzyloxycarbonyl-N-methylamino)propyl]-5-n-butyl-2,4-dihydro-4-[[2'-(5-tetrazolyl)biphenyl-4-yl]methyl]-3H-triazol-3-one (Example 10)

2-[3-(N-Benzyl-N-benzyloxycarbonylamino)propyl]-5-n-butyl-2,4-dihydro-4-[[2'-(5-tetrazolyl)biphenyl-4-yl]methyl]-3-triazol-3-one (Example 11)

4-[[2'-(N-Benzoylsulfamoyl)biphenyl-4-yl) methyl]-5-n-butyl-2,4-dihydro-2-isopropyl-3H-1,2,4-triazol-3-one (Example 12)

4-[[2'-(N-Benzoylsulfamoyl)biphenyl-4-yl]methyl]-5-n-butyl-2-(2-chlorophenyl)-2,4-dihydro-3H-1,2,4-triazol-3-one (Example 13)

5-n-Butyl-2-(2-chlorophenyl)-2,4-dihydro-4-[[2'-[N-(tri-fluoroacetyl)sulfamoyl]biphenyl-4-yl]methyl]-3H-1,2,4-triazol-3-one (Example 15)

4-[[2'-(N-Benzoylsulfamoyl)biphenyl)-4-yl]methyl]-5-n-butyl-2,4-dihydro-2-[2-(trifluoromethyl)phenyl]-3H-1,2,4-triazol-3-one (Example 16)

5-n-Butyl-2,4-dihydro-4-[[2'-[N-(trifluoroacetyl)sulfamoyl]biphenyl-4-yl]methyl]-2-[2-(trifluoromethyl)phenyl]-3H-1,2,4-triazol-3-one (Example 17)

5-n-Butyl-2,4-dihydro-4-[[2'-[N-(4-fluorobenzoyl)sulfamoyl]biphenyl-4-yl]methyl]-2-[2-(trifluoromethyl)phenyl]-3H-1,2,4-triazol-3-one (Example 18)

5-n-Butyl-2,4-dihydro-4-[[2'-(N-octanoylsulfamoyl)biphenyl-4-yl]methyl]-2-[2-(trifluoromethyl)phenyl]-3H-1,2,4-triazol-3-one (Example 19)

5-n-Butyl-4-[[2'-[N-(3-cyclopentylpropionyl)sulfamoyl]biphenyl-4-yl]methyl]-2,4-dihydro-2-[2-(trifluoromethyl)phenyl]-3H-1,2,4-triazol-3-one (Example 20)

5-n-Butyl-4-[[2'-[N-(cyclopropanecarbonyl)sulfamoyl]biphenyl-4-yl]methyl]-2,4-dihydro-2-[2-(trifluoromethyl)phenyl]-3H-1,2,4-triazol-3-one (Example 21)

5-n-Butyl-2,4-dihydro-4-[[2'-[N-(diphenylacetyl)sulfamoyl]biphenyl-4-yl]methyl]-2-[2-(trifluoromethyl)phenyl]-3H-1,2,4-triazol-3-one (Example 22)

5-n-Butyl-2,4-dihydro-4-[[2'-[N-(4-morpholinecarbonyl)sulfamoyl]biphenyl-4-yl]methyl]-2-[2-(trifluoromethyl)phenyl]-3H-1,2,4-triazol-3-one (Example 23)

5-n-Butyl-2-($\alpha$-carboxybenzyl)-2,4-dihydro-4-[[2'-(5-tetrazolyl)biphenyl-4-yl]methyl]-3H-1,2,4-triazol-3-one (Example 28)

5-n-Butyl-2-cyanomethyl-2,4-dihydro-4-[[2'-(5-tetrazolyl)biphenyl-4-yl]methyl]-3H-1,2,4-triazol-3-one (Example 29)

5-n-Butyl-2,4-dihydro-2-(1-phenylpropyl)-4-[[2'-(5-tetrazolyl)biphenyl-4-yl]methyl]-3H-1,2,4-triazol-3-one (Example 30)

5-n-Butyl-2,4-dihydro-2-[1-(N-methylcarbamoyl)ethyl]-4-[[2'-(5-tetrazolyl)biphenyl-4-yl]methyl]-3H-1,2,4-triazol-3-one (Example 31)

5-n-Butyl-2,4-dihydro-2-phenacyl-4-[[2'-(5-tetrazolyl)biphenyl-4-yl]methyl)-3H-1,2,4-triazol-3-one (Example 32)

5-n-Butyl-2-(4-chlorophenoxymethyl)-2,4-dihydro-4-[[2'-(5-tetrazolyl)biphenyl-4-yl]methyl]-3H-1,2,4-triazol-3-one (Example 33)

5-n-Butyl-2,4-dihydro-2-(phenylthiomethyl)-4-[[2'-(5-tetrazolyl)biphenyl-4-yl]methyl]-3H-1,2,4-triazol-3-one (Example 34)

2,4-Bis[[2'-(N-trityltetrazol-5-yl)biphenyl-4-yl]methyl]-5-n-butyl-2,4-dihydro-3H-1,2,4-triazol-3-one (Example 35)

5-n-Butyl-2-cyclopropyl-2,4-dihydro-4-[[2'-(5-tetrazolyl)biphenyl-4-yl]methyl]-3H-1,2,4-triazol-3-one (Example 36)

5-n-Butyl-2,4-dihydro-2-[3-(N-methyl-N-phenylcarbamoyloxy)propyl]-4-[[2'-(5-tetrazolyl)biphenyl-4-yl]methyl]-3H-1,2,4-triazol-3-one (Example 37)

5-n-Butyl-2-[1-(carbomethoxy)isobutyl]-2,4-dihydro-4-[[2'-(5-tetrazolyl)biphenyl-4-yl]methyl]-3H-1,2,4-triazol-3-one (Example 38)

5-n-Butyl-2-(1-carboxyisobutyl)-2,4-dihydro-4-[[2'-(5-tetrazolyl)biphenyl-4-yl]methyl]-3H-1,2,4-triazol-3-one (Example 39)

5-Cyclopropyl-2,4-dihydro-2-(2-nitrophenyl)-4-[[2'-(5-tetrazolyl)biphenyl-4-yl]methyl]-3H-1,2,4-triazol-3-one (Example 40)

2-(2-Chlorophenyl)-2,4-dihydro-5-(3-methylbutyl)-4-[[2'-(5-tetrazolyl)biphenyl-4-yl]methyl]-3H-1,2,4-triazol-3-one (Example 41)

2-[4-(Benzyloxy)phenyl]-5-n-butyl-2,4-dihydro-4-[[2'-(5-tetrazolyl)biphenyl-4-yl]methyl]-3H-1,2,4-triazol-3-one (Example 42)

The following representative compounds of formula (I) can be prepared using the procedures of the foregoing Examples and Reaction Schemes:

(1) 5-n-butyl-2-[2-(carboxymethyl)phenyl]-2,4-dihydro-4-[[2'-(5-tetrazolyl)biphenyl-4-yl]methyl]-3H-1,2,4-triazol-3-one;

(2) 5-n-butyl-2,4-dihydro-2-[2-(2-oxazolin-2-yl)phenyl]-4-[[2'-(5-tetrazolyl)biphenyl-4-yl]methyl]-3H-1,2,4-triazol-3-one;

(3) 2-benzyl-5-n-butyl-2,4-dihydro-4-[[2'-(5-tetrazolyl)biphenyl-4-yl]methyl]-3H-1,2,4-triazole-3-thione;

(4) 5-n-butyl-2-(2-chlorophenyl)-2,4-dihydro-4-[[2'-(5-tetrazolyl)biphenyl-4-yl]methyl]-3H-1,2,4-triazole-3-thione;

(5) 5-n-butyl-2,4-dihydro-2-isopropyl-$N^3$-phenyl-4-[[2'-(5-tetrazolyl)biphenyl-4-yl]methyl]-3H-1,2,4-triazol-3-imine;

(6) 2-(2-chlorophenyl)-2,4-dihydro-5-(n-propylthio)-4-[[2'-(5-tetrazolyl)biphenyl-4-yl]methyl]-3H-1,2,4-triazol-3-one;

(7) 4-[[2'-[N-(benzenesulfonyl)carbamoyl]biphenyl-4-yl]methyl]-5-n-butyl-2,4-dihydro-2-[2-(trifluoromethyl)phenyl]-3H-1,2,4-triazol-3-one;

(8) 5-n-butyl-2-(2-chlorophenyl)-2,4-dihydro-4-[[2'-[N-(2-pyrimidyl)sulfamoyl]biphenyl-4-yl]methyl-3H-1,2,4-triazol-3-one;

(9) 5-n-butyl-4-[[2'-[N-(cyclopropanecarbonyl)sulfamoyl]biphenyl-4-yl]methyl]-2-(2,6-dichlorophenyl)-2,4-dihydro-3H-1,2,4-triazol-3-one;

(10) 5-n-butyl-4-[[2'-[N-(cyclopropanecarbonyl)sulfamoyl]biphenyl-4-yl]methyl]-2,4-dihydro-2-phenethyl-3H-1,2,4-triazol-3-one;

(11) 5-n-butyl-4-[[2'-[N-(cyclopropanecarbonyl)sulfamoyl]biphenyl-4-yl]methyl]-2,4-dihydro-2-[2-(trifluoromethyl)phenyl]-3H-1,2,4-triazol-3-one;

(12) 5-n-butyl-4-[[2'-[N-(cyclopropanecarbonyl)sulfamoyl]biphenyl-4-yl]methyl]-2,4-dihydro-$N^3$-methyl-2-[2-(trifluoromethyl)phenyl]-3H-1,2,4-triazol-3-imine;

(13) 4-[[2'-[N-(cyclopropanecarbonyl)sulfamoyl]biphenyl-4-yl]methyl]-2,4-dihydro-5-n-propyl-2-[2-(trifluoromethyl)phenyl]-3H-1,2,4-triazol-3-one;

(14) 4-[[2'-[N-(cyclopropanecarbonyl)sulfamoyl]biphenyl-4-yl]methyl]-2,4-dihydro-5-[(2-methylcyclopropyl)methyl]-2-[2-(trifluoromethyl)phenyl]-3H-1,2,4-triazol-3-one;

(15) 4-[[2'-[N-(cyclopropanecarbonyl)sulfamoyl]biphenyl-4-yl]methyl]-2,4-dihydro-5-(4,4,4-trifluorobutyl)-2-[2-(trifluoromethyl)phenyl]-3H-1,2,4-triazol-3-one;

(16) 5-n-butyl-4-[[2'-[N-[4-(carbomethoxy)butyryl]sulfamoyl]biphenyl-4-yl]methyl]-2,4-dihydro-2-[2-(trifluoromethyl)phenyl]-3H-1,2,4-triazol-3-one;

(17) 5-n-butyl-2,4-dihydro-4-[[2'-(N-glutarylsulfamoyl)biphenyl-4-yl]methyl]-2-[2-(trifluoromethyl)phenyl]-3H-1,2,4-triazol-3-one.

What is claimed is:

1. A method of treating, psychoses, a central nervous system disorder which comprises administering to a patient in need of such treatment a therapeutically effective amount of a compound of structural formula:

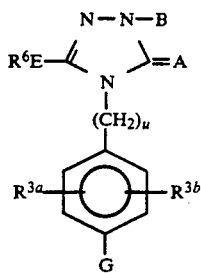 (I)

or a pharmaceutically acceptable salt thereof, wherein:

G is $R^1$ or

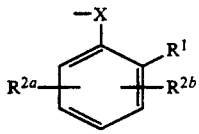

$R^1$ is
(a) —$NHSO_2R^{23}$,
(b) —$NHSO_2NHCOR^{23}$,
(c) —$NHCONHSO_2R^{23}$,
(d) —$SO_2NHR^{23}$,
(e) —$SO_2$—$NHCOR^{23}$,
(f) —$SO_2NHCOR^{23}R^{24}$,
(g) —$SO_2NHCOOR^{23}$,
(h) —$SO_2NHOR^{23}$,
(i) —$CH_2SO_2NHCOR^{23}$,
(j) —$CH_2SO_2NHCONHR^{23}$, or
(k) —$CO_2H$;

$R^{2a}$ and $R^{2b}$ are each independently:
(a) hydrogen,
(b) —Cl, —Br, —I, or —F
(c) —$CF_3$,
(d) $C_1$-$C_4$-alkyl, or
(e) $C_1$-$C_4$-alkoxy;

$R^{3a}$ is
(a) —H,
(b) —Cl, —Br, —I, or —F
(c) $C_1$-$C_6$-alkyl,
(d) $C_1$-$C_6$-alkoxy, or
(e) $C_1$-$C_6$-alkoxy-$C_1$-$C_4$-alkyl;

$R^{3b}$ is
(a) —H,
(b) —Cl, —Br, —I, or —F
(c) $C_1$-$C_6$-alkyl,
(d) $C_1$-$C_5$-alkylcarbonyloxy,
(e) $C_3$-$C_6$-cycloalkyl
(f) $C_1$-$C_6$-alkoxy, or
(g) $CF_3$;

$R^4$ is H, $C_1$-$C_6$ alkyl, —$CH_2$-aryl or aryl wherein aryl is phenyl or naphthyl unsubstituted or substituted with one or two substituents selected from the group consisting of: —Cl, —Br, —I, —F, $C_1$-$C_4$-alkyl, $C_1$-$C_4$-alkoxy, $NO_2$, $CF_3$, $C_1$-$C_4$-alkylthio, —OH, —$NH_2$, —$CO_2H$, —$CO_2$—$C_1$-$C_4$-alkyl, —CN and —$NHCOR^9$;

$R^5$ is H or —$CH(R^4)$—O—CO—$R^{4a}$, wherein $R^{4a}$ is $C_1$-$C_6$-alkyl, aryl or —$CH_2$-aryl;

E is a single bond, —$NR^{13}(CH_2)_s$—, —$S(O)_x(CH_2)_s$— where x is 0 to 2 and s is 0 to 5, —CH(OH)—, —$O(CH_2)_s$—, —CO—;

$R^6$ is (a) phenyl, unsubstituted or substituted with 1 or 2 substituents selected from the group consisting of Cl, Br, I, F, —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, $C_3$-$C_7$-cycloalkyl, and $C_3$-$C_{10}$-alkenyl;

(b) $C_1$-$C_6$-alkyl, $C_2$-$C_6$-alkenyl or $C_2$-$C_6$-alkynyl each of which is unsubstituted or substituted with one or more substituents selected from the group consisting of: aryl, $C_3$-$C_7$-cyclo-alkyl, Cl, Br, I, F, —OH, —O—$C_1$-$C_4$-alkyl, —$NH_2$, —$NH(C_1$-$C_4$-alkyl), —$N(C_1$-$C_4$-alkyl)$_2$, —NH—$SO_2R^4$, —$COOR^4$, —$SO_2NHR^9$, and —S—$C_1$-$C_4$-alkyl;

(c) mono-, di-, tri- or polyfluoro-$C_1$-$C_5$-alkyl;

(d) $C_3$-$C_7$-cycloalkyl, unsubstituted or substituted with one or more substituents selected from the group consisting of $C_1$-$C_4$-alkyl, O—$C_1$-$C_4$-alkyl, S—$C_1$-$C_4$-alkyl, OH, perfluoro-$C_1$-$C_4$-alkyl, Cl, Br, F, and I; or (e) $C_3$-$C_7$-cycloalkyl-$C_1$-$C_3$-alkyl, wherein the cycloalkyl is unsubstituted or substituted as in (e) above;

A is =O, =S or =$NR^{21}$;

B is
(a) H provided A is not $NR^{21}$;
(b) $C_1$-$C_{10}$-alkyl;
(c) substituted $C_1$-$C_{10}$-alkyl in which one or more substituent(s) is selected from the group consisting of:
(1) I, Br, Cl, or F,
(2) hydroxy,
(3) $C_1$-$C_{10}$-alkoxy,
(4) $C_1$-$C_5$-alkoxycarbonyl,
(5) $C_1$-$C_4$-alkylcarbonyloxy,
(6) $C_3$-$C_8$-cycloalkyl,
(7) phenyl, naphthyl or biphenyl,
(8) substituted phenyl, naphthyl or biphenyl in which the substituents are $V_1$, $V_2$, $V_3$, $V_4$ and $V_5$,
(9) $C_1$-$C_{10}$-alkyl-$S(O)_p$ in which p is 0 to 2,
(10) $C_3$-$C_8$-cycloalkyl-$S(O)_p$,
(11) phenyl-$S(O)_p$,
(12) substituted phenyl-$S(O)_p$ in which the substituents are $V_1$-$V_5$,
(13) oxo,
(14) carboxy,
(15) $NR^9R^9$,
(16) $C_1$-$C_5$-alkylaminocarbonyl,
(17) di($C_1$-$C_5$-alkyl)aminocarbonyl,
(18) cyano,
(19) —$OCONR^{21}R^{22}$,
(20) —$NR^{21}COR^{22}$,
(21) —$NR^{21}CO_2R^{22}$, or
(22) —$NR^{21}CONR^{21}R^{22}$;

(d) $C_2$-$C_{10}$-alkenyl,
(e) $C_2$-$C_{10}$-alkynyl,
(f) $C_3$-$C_8$-cycloalkyl,
(g) substituted $C_3$-$C_8$-cycloalkyl or substituted $C_3$-$C_8$-cycloalkyl-$C_1$-$C_4$-alkyl having one or more substituents selected from the group consisting of:
(1) Cl, Br, F, or I,
(2) hydroxy,
(3) $C_1$-$C_6$-alkyl,
(4) $C_1$-$C_6$-alkoxy,
(5) $C_1$-$C_4$-alkylcarbonyloxy,
(6) $C_1$-$C_5$-alkoxycarbonyl, (7) carboxy,
(8) oxo,
(9) $C_1-C_5$-alkylaminocarbonyl,
(10) di($C_1-C_5$-alkyl)aminocarbonyl,
(11) $C_1-C_4$-alkylcarbonyl,
(12) phenyl, naphthyl or biphenyl,
(13) substituted phenyl, naphthyl or biphenyl in which the substituents are $V_1$, $V_2$, $V_3$, $V_4$ and $V_5$,
(14) —$NR^{21}COR^{22}$,
(15) —$NR^{21}CO_2R^{22}$,
(16) —$OCONR^{21}R^{22}$, and
(17) —CN;

(h) phenyl, naphthyl or biphenyl,
(i) substituted phenyl, naphthyl or biphenyl in which the substituents are $V_1$, $V_2$, $V_3$, $V_4$ and $V_5$,
(j) phenyl—$(CH_2)_r$—$(Q)_c$—$(CH_2)_t$—,
(k) substituted phenyl—$(CH_2)_r$—$(Q)_c$—$(CH_2)_t$— in which the phenyl group is substituted with $V_1$, $V_2$, $V_3$, $V_4$ and $V_5$,

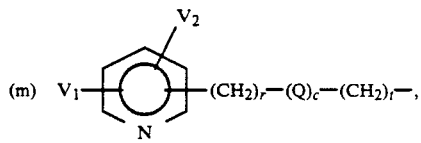

(m) 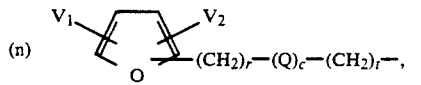

(n) 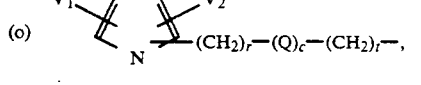

(o) 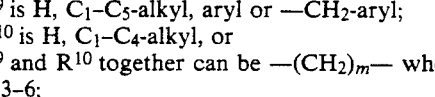

$R^9$ is H, $C_1-C_5$-alkyl, aryl or —$CH_2$-aryl;
$R^{10}$ is H, $C_1-C_4$-alkyl, or
$R^9$ and $R^{10}$ together can be —$(CH_2)_m$— where m is 3-6;
$R^{11}$ is H, $C_1-C_6$-alkyl, $C_2-C_4$-alkenyl, $C_1-C_4$-alkoxy-$C_1-C_4$-alkyl, or —$CH_2$—$C_6H_4R^{20}$;
$R^{12}$ is —CN, —$NO_2$ or —$CO_2R^4$;
$R^{13}$ is H, $C_2-C_4$-alkanoyl, $C_1-C_6$-alkyl, allyl, $C_3-C_6$-cycloalkyl, phenyl or benzyl;
$R^{14}$ is H, $C_1-C_8$-alkyl, $C_1-C_8$-perfluoroalkyl, $C_3-C_6$-cycloalkyl, phenyl or benzyl;
$R^{15}$ is H, $C_1-C_6$-alkyl, hydroxy;
$R^{16}$ is H, $C_1-C_6$-alkyl, $C_3-C_6$-cycloalkyl, phenyl or benzyl;
$R^{17}$ is —$NR^9R^{10}$, —$OR^{10}$, —$NHCONH_2$, —$NHCSNH_2$, —$NHSO_2CF_3$,

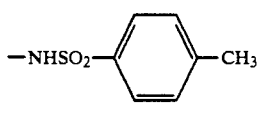

or

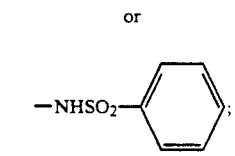

$R^{18}$ and $R^{19}$ are independently $C_1-C_4$-alkyl or taken together are —$(CH_2)_q$— where q is 2 or 3;
$R^{20}$ is H, —$NO_2$, —$NH_2$, —OH or —$OCH_3$;

$R^{21}$ is
(a) H,
(b) phenyl, unsubstituted or substituted with 1 or 2 substituents selected from the group consisting of: Cl, Br, I, F, —O—$C_1-C_4$-alkyl, $C_1-C_4$-alkyl, —$NO_2$, —$CF_3$, —$SO_2NR^9R^{10}$, —S—$C_1-C_4$-alkyl, —OH, —$NH_2$, —$COOR^4$, $C_3-C_7$-cycloalkyl and $C_3-C_{10}$-alkenyl;
(c) $C_1-C_6$-alkyl, $C_2-C_6$-alkenyl or $C_2-C_6$-alkynyl each of which is unsubstituted or substituted with one or more substituents selected from the group consisting of aryl, $C_3-C_7$-cyclo-alkyl, Cl, Br, I, F, —OH, —O—$C_1-C_4$-alkyl, —$NH_2$, —NH($C_1-C_4$-alkyl), —N($C_1-C_4$-alkyl)$_2$, —NH—$SO_2R^4$, —$COOR^4$, —$SO_2NHR^9$, and —S—$C_1-C_4$-alkyl;
(d) $C_3-C_7$-cycloalkyl, unsubstituted or substituted with one or more substituents selected from the group consisting of: $C_1-C_4$-alkyl, —O—$C_1-C_4$-alkyl, —S—$C_1-C_4$-alkyl, —OH, —$COOR^4$, $C_1-C_4$-perfluoroalkyl, Cl, Br, F, and I, or
(e) ($C_1-C_4$)-perfluoroalkyl;
$R^{22}$ is $R^{21}$ excluding H;
$R^{23}$ is
(a) aryl,
(b) heteroaryl, wherein heteroaryl is defined as pyridine and which can be unsubstituted, monosubstituted or disubstituted with substituents selected from the group consisting of —OH, —SH, $C_1-C_4$-alkyl, $C_1-C_4$-alkoxy, —$CF_3$, Cl, Br, F, I, —$NO_2$ —$CO_2H$, —$CO_2$—$C_1-C_4$-alkyl, —$NH_2$, —NH($C_1-C_4$-alkyl) and —N($C_1-C_4$-alkyl)$_2$;
(c) $C_3-C_7$-cycloalkyl optionally substituted with one or more substituents selected from the group consisting of $C_1-C_4$-alkyl, —O—$C_1-C_4$-alkyl, —S—$C_1-C_4$-alkyl, —OH, —$COOR^4$, perfluoro-$C_1-C_4$-alkyl, Cl, Br, F, and I;
(d) $C_1-C_8$-alkyl unsubstituted or substituted with one or two substituents selected from the group consisting of: aryl, heteroaryl, —OH, —SH, $C_1-C_4$-alkyl, $C_2-C_4$-alkenyl, $C_2-C_4$-alkynyl, —O($C_1-C_4$-alkyl), S($C_1-C_4$-alkyl), —$C_3-C_8$-cycloalkyl, —$CF_3$, Cl, Br, F, I, —$NO_2$, —$CO_2H$, —$CO_2$—$C_1-C_4$-alkyl, —$PO_3H$, —PO(OH) (O—$C_1-C_4$-alkyl), —PO($OR^4$) ($R^9$), —$NH_2$, —NH($C_1-C_4$-alkyl), —N($C_1-C_4$-alkyl)$_2$, —NH-aryl, —N(aryl)$_2$, —N($CH_2CH_2$)$_2$L —$NR^4COR^{22}$, —$CONR^4R^{22}$, —$OCONR^4R^{22}$, $SO_2NR^4R^{22}$, —$NR^4SO_2R^{22}$,
(e) polyfluoro-$C_1-C_4$-alkyl;
(f) —$NR^{21}R^{21}$, or
(g) —N($CH_2CH_2$)L;
X is
(a) a single bond,
(b) —CO—,
(c) —O—,
(d) —S—, (e) —N—,
   |
   $R^{13}$ (f) —CON—,
   |
   $R^{15}$ -continued (g) —NCO—,
     |
     R$^{15}$ (h) —OCH$_2$—,
(i) —CH$_2$O—
(j) —SCH$_2$—,
(k) —CH$_2$S—,
(l) —NHC(R$^9$)(R$^{10}$)—,
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,
(v) 1,1-dimethylcyclopropyl or 1,2-dimethylcyclopropyl, (w) 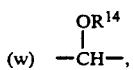

(x) 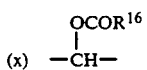

(y) 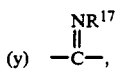

or (z) 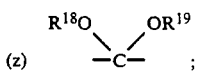 ;

Q is —C(O)—, —S—, —O— or —NR$^4$;
c is 0 or 1;
r and t are 0 to 2;
V$_1$, V$_2$, V$_3$, V$_4$ and V$_5$ are each independently selected from:
  (a) H,
  (b) C$_1$-C$_5$-alkoxy,
  (c) C$_1$-C$_5$-alkyl,
  (d) hydroxy,
  (e) C$_1$-C$_5$-alkyl-S(O)$_p$,
  (f) —CN,
  (g) —NO$_2$,
  (h) —NR$^9$R$^{10}$;
  (i) C$_1$-C$_5$-alkyl-CONR$^9$R$^{10}$,
  (j) —CONR$^9$R$^{10}$,
  (k) —CO$_2$R$^9$,
  (l) C$_1$-C$_5$-alkyl-carbonyl,
  (m) CF$_3$,
  (n) I, Br, Cl, F,
  (o) hydroxy-C$_1$-C$_4$-alkyl-,
  (p) carboxy-C$_1$-C$_4$-alkyl-,
  (q) —NH—SO$_2$CF$_3$,
  (r) aryl,
  (s) C$_1$-C$_5$-alkyl-CO$_2$R$^9$,
  (t) aryloxy,
  (u) aryl-C$_1$-C$_3$-alkoxy,
  (v) aryl-C$_1$-C$_3$-alkyl,
  (w) carboxyphenyl,
  (x) —(CH$_2$)$_r$OCOR$^{22}$,
  (y) —(CH$_2$)$_r$OCONR$^{21}$R$^{22}$,
  (z) —(CH$_2$)$_r$NR$^{21}$COR$^{22}$,
  (aa) —(CH$_2$)$_t$NR$^{21}$CO$_2$R$^{22}$, or
  (bb) —(CH$_2$)$_t$NR$^{21}$CONR$^{23}$R$^{22}$;
u is 1 or 2;
Z is O, NR$^{13}$ or S.

2. The method of claim 1 wherein:
R$^1$ is
  (a) —NHSO$_2$R$^{23}$,
  (b) —NHSO$_2$NHCOR$^{23}$,
  (c) —NHCONHSO$_2$R$^{23}$,
  (d) —SO$_2$NHR$^{23}$,
  (e) —SO$_2$NHCOR$^{23}$,
  (f) —SO$_2$NHCONR$^{24}$R$^{23}$,
  (g) —SO$_2$NHCOOR$^{23}$
  (h) —SO$_2$NHOR$^{23}$,
  (i) —CH$_2$SO$_2$NHCOR$^{23}$, or
  (j) —CH$_2$SO$_2$NHCONHR$^{23}$;
R$^{2a}$ is H;
R$^{2b}$ is H, F, Cl, CF$_3$ or C$_1$-C$_4$-alkyl;
R$^{3a}$ is H;
R$^{3b}$ is H, F, Cl, CF$_3$, C$_1$-C$_4$-alkyl, C$_1$-C$_4$-alkoxy, C$_1$-C$_4$-alkylthio, —SO$_2$—CH$_3$, NH$_2$, —N(C$_1$-C$_4$-alkyl)$_2$ or NO$_2$;
E is a single bond, —O— or —S—;
R$^6$ is
  (a) C$_1$-C$_6$-alkyl unsubstituted or substituted with a substituent selected from the group consisting of: Cl, F, CF$_3$, —OH, —O—CH$_3$, —OC$_2$H$_5$, —S—CH$_3$, —S—C$_2$H$_5$, phenyl, cyclopropyl, or C$_1$-C$_2$-alkylcyclopropyl
  (b) C$_2$-C$_6$-alkenyl or C$_2$-C$_6$-alkynyl;
  (c) phenyl, unsubstituted or substituted with Cl, F, Br, I, —CF$_3$, —NO$_2$, —OH, —NH$_2$, —S—CH$_3$, —S—C$_2$H$_5$, —SO$_2$NH$_2$, —O—CH$_3$;
  (e) perfluoro-C$_1$-C$_4$-alkyl which is a member selected from the group consisting of CF$_3$—, CF$_3$CF$_2$—, CF$_3$CF$_2$CF$_2$—, or CF$_3$CF$_2$CF$_2$CF$_2$—;
  (f) C$_3$-C$_7$-cycloalkyl unsubstituted or substituted with methyl, ethyl, CF$_3$ or CF$_3$CF$_2$;
A is =O, =S or =NR$^{21}$;
B is
  (a) H provided A is not NR$^{21}$,
  (b) C$_1$-C$_{10}$-alkyl,
  (c) substituted C$_1$-C$_{10}$-alkyl in which one or two substituents are selected from:
    (1) hydroxy,
    (2) C$_1$-C$_5$-alkoxy,
    (3) C$_1$-C$_5$-alkoxycarbonyl,
    (4) C$_1$-C$_4$-alkylcarbonyloxy,
    (5) C$_3$-C$_8$-cycloalkyl,
    (6) phenyl, naphthyl or biphenyl,
    (7) substituted phenyl, naphthyl or biphenyl in which the substituents are V$_1$, V$_2$, V$_3$, V$_4$ and V$_5$,
    (8) C$_1$-C$_5$-alkyl-S(O)$_p$,
    (9) phenyl-S(O)$_p$
    (10) substituted phenyl-S(O)$_p$ in which the substituent is V$_1$
    (11) oxo,
    (12) carboxy,
    (13) C$_1$-C$_5$-alkylaminocarbonyl;
    (14) —NR$^{21}$COR$^{22}$,
    (15) —NR$^{21}$CO$_2$R$^{22}$,
    (16) —NR$^{21}$CONR$^{21}$R$^{22}$,
    (17) —OCONR$^{21}$R$^{22}$,
    (18) —CN;
  (d) mono-, di-, tri-, or polyfluoro-C$_1$-C$_{10}$-alkyl, (e) $C_2$-$C_{10}$-alkenyl,
(f) $C_2$-$C_{10}$-alkynyl,
(g) $C_3$-$C_8$-cycloalkyl,
(h) substituted $C_3$-$C_8$-cycloalkyl or substituted $C_3$-$C_8$-cycloalkyl-$C_1$-$C_4$-alkyl in which one or more substituent(s) is selected from:
 (1) hydroxy,
 (2) $C_1$-$C_5$-alkoxy,
 (3) $C_1$-$C_5$-alkoxycarbonyl,
 (4) $C_1$-$C_5$-alkylcarbonyloxy,
 (5) $C_1$-$C_6$-alkyl,
 (6) phenyl, naphthyl or biphenyl,
 (7) substituted phenyl, naphthyl or biphenyl in which the substituents are $V_1$, $V_2$, $V_3$, $V_4$, and $V_5$,
 (8) oxo,
 (9) carboxy,
 (10) $C_1$-$C_5$-alkylaminocarbonyl,
 (11) $-NR^{21}COR^{22}$,
 (12) $-NR^{21}CO_2R^{22}$,
 (13) $-OCONR^{21}R^{22}$, and
 (14) $-CN$,
(i) phenyl, naphthyl or biphenyl,
(j) substituted phenyl, naphthyl or biphenyl in which the substituents are $V_1$, $V_2$, $V_3$, $V_4$ and $V_5$,
(k) phenyl-$(CH_2)_r$—$(Q)_c$—$(CH_2)_t$—,
(l) substituted phenyl-$(CH_2)_r$—$(Q)_c$—$(CH_2)_t$— wherein the substituents are $V_1$, $V_2$, $V_3$, $V_4$ and $V_5$, (m) 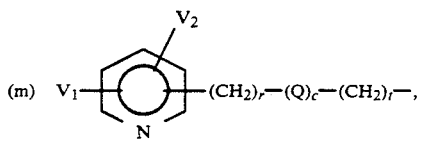

(n) 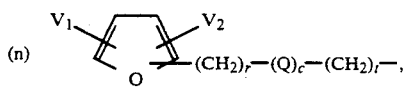

(o) 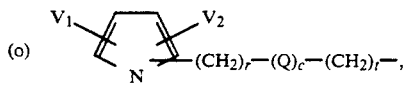

$V_1$, $V_2$, $V_3$, $V_4$ and $V_5$ are independently selected from:
 (a) hydrogen,
 (b) $C_1$-$C_5$-alkoxy,
 (c) $C_1$-$C_5$-alkyl,
 (d) hydroxy,
 (e) $NR^9R^{10}$,
 (f) $CO_2R^9$,
 (g) trifluoromethyl,
 (h) Cl, Br, I, F,
 (i) hydroxy-$C_1$-$C_4$-alkyl,
 (j) $-NH-SO_2CF_3$,
 (k) CN,
 (l) $NO_2$,
 (m) $C_1$-$C_5$-alkyl-$CO_2R^9$,
 (n) aryl,
 (o) aryl-$C_1$-$C_3$-alkyl,
 (p) $C_1$-$C_5$-alkyl-$CONR^9R^{10}$,
 (q) $-CONR^9R^{10}$,
 (r) $C_1$-$C_5$-alkyl-$S(O)_p$,
 (s) $(CH_2)_tOCOR^{22}$,
 (t) $(CH_2)_tNR^{21}COR^{22}$,
 (u) $(CH_2)_tNR^{21}COR^{22}$,
 (v) $(CH_2)_tNR^{21}CONR^{21}R^{22}$, or
 (w) aryl-$C_1$-$C_3$-alkoxy;
u is 1; and
X is:
 (a) a single bond,
 (b) $-C(O)-$, or
 (c) $-NR^{15}C(O)-$.

3. The method of claim 2 wherein:
E is a single bond or $-S-$;
$R^1$ is
 (a) $-SO_2NHCOR^{23}$,
 (b) $-SO_2NHCONR^{24}R^{23}$,
 (c) $-SO_2NHCOOR^{23}$
 (d) $-SO_2NHOR^{23}$, or
 (e) $-CH_2SO_2NHCOR^{23}$;
$R^6$ is
 (a) $C_1$-$C_6$-alkyl unsubstituted or substituted with $-F$, $-CF_3$, cyclopropyl, or $C_1$-$C_2$-alkyl-cyclopropyl or
 (b) cyclopropyl, unsubstituted or substituted with $-CH_3$, $-C_2H_5$, $-CF_3$ or $-CF_2CF_3$;
A is $=O$, $=S$ or $=NR^{21}$;
B is
 (a) H provided A is not $NR^{21}$,
 (b) $C_1$-$C_{10}$-alkyl,
 (c) $C_3$-$C_8$-cycloalkyl,
 (d) $C_3$-$C_8$-cycloalkyl-$C_1$-$C_4$-alkyl,
 (e) substituted $C_1$-$C_{10}$-alkyl, $C_3$-$C_8$-cycloalkyl, or $C_3$-$C_8$-cycloalkyl-$C_1$-$C_4$-alkyl each of which can have one or two substituents selected from the group consisting of:
  (1) hydroxy,
  (2) $C_1$-$C_5$-alkoxy,
  (3) $C_1$-$C_5$-alkoxycarbonyl,
  (4) phenyl, naphthyl or biphenyl,
  (5) substituted phenyl, naphthyl or biphenyl wherein the substituents are $V_1$, $V_2$, $V_3$, $V_4$, and $V_5$,
  (6) carboxy,
  (7) $C_1$-$C_5$-alkylaminocarbonyl,
  (8) oxo,
  (9) $-NR^{21}COR^{22}$,
  (10) $-NR^{21}CO_2R^{22}$,
  (11) $-OCONR^{21}R^{22}$, or
  (12) $-CN$,
 (f) mono-, di-, tri-, or polyfluoro-$C_1$-$C_{10}$-alkyl,
 (g) phenyl, naphthyl or biphenyl
 (h) phenyl, naphthyl or biphenyl substituted with $V_1$, $V_2$, $V_3$, $V_4$ and $V_5$,
 (i) phenyl-$(CH_2)_r$—$(Q)_c$—$(CH_2)_t$—,
 (j) substituted phenyl-$(CH_2)_r$—$(Q)_c$—$(CH_2)_t$— in which the phenyl is substituted with $V_1$, $V_2$, $V_3$, $V_4$ and $V_5$, (k) 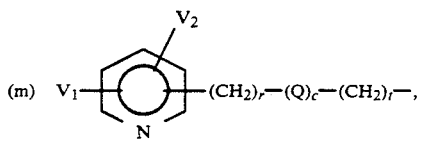

or (l) 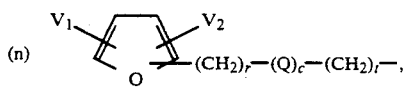

$V_1$, $V_2$, $V_3$, $V_4$ and $V_5$ are selected from:
 (a) hydrogen, (b) $C_1$-$C_5$-alkyl,
(c) $C_1$-$C_5$-alkoxy,
(d) $CO_2R^9$,
(e) Cl, Br, F, I,
(f) hydroxy-$C_1$-$C_4$-alkyl-,
(g) $C_1$-$C_5$-alkyl-$CO_2R^9$,
(h) $C_1$-$C_5$-alkyl-$CONR^9R^{10}$,
(i) $CONR^9R^{10}$,
(j) CN,
(k) $NO_2$,
(l) $CF_3$,
(m) aryl,
(n) $C_1$-$C_5$-alkyl-$S(O)_p$,
(o) $(CH_2)_tOCOR^{22}$,
(p) $(CH_2)_tNR^{21}COR^{22}$,
(q) $(CH_2)_tNR^{21}CO_2R^{22}$,
(r) hydroxy,
(s) $NR^9R^{10}$,
(t) aryl-$C_1$-$C_3$-alkyl or
(u) aryl-$C_1$-$C_3$-alkoxy.

4. The method as recited in claim 3 wherein:
G is

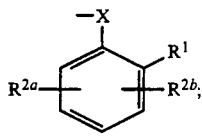

$R^1$ is —$SO_2NHCOR^{23}$, —$SO_2NHCONR^{24}R^{23}$, —$SO_2NHCOOR^{23}$, —$SO_2NHOR^{23}$, or —$CH_2SO_2NHCOR^{23}$;
$R^{2a}$, $R^{2b}$, $R^{3a}$, and $R^{3b}$ are each H; and
X is a single bond.

5. The method as recited in claim 4 wherein:
G is $R^1$;
$R^1$ is —$SO_2NHCOR^{23}$, —$SO_2NHCONR^{24}R^{23}$, —$SO_2NHCOOR^{23}$, —$SO_2NHOR^{23}$, or —$CH_2SO_2NHCOR^{23}$;
$R^{3a}$ is H;
$R^{3b}$ is H, F, Cl, $CF_3$, $CH_3$, $OCH_3$, or $NO_2$.

6. A pharmaceutical composition useful in the treatment of psychoses, a central nervous system disorder, which comprises a pharmaceutically acceptable carrier and a pharmaceutically effective amount of a compound as recited in claim 1.

7. A method of achieving neurotensin receptor blockade by administering to a patient in need of such treatment a therapeutically effective amount of a compound of structural formula:

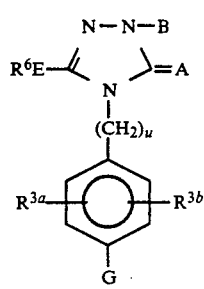

(I)

or a pharmaceutically acceptable salt thereof, wherein:
G is $R^1$ or

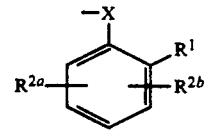

$R^1$ is
(a) —$NHSO_2R^{23}$,
(b) —$NHSO_2NHCOR^{23}$,
(c) —$NHCONHSO_2R^{23}$,
(d) —$SO_2NHR^{23}$,
(e) —$SO_2$—$NHCOR^{23}$,
(f) —$SO_2NHCOR^{23}R^{24}$,
(g) —$SO_2NHCOOR^{23}$,
(h) —$SO_2NHOR^{23}$,
(i) —$CH_2SO_2NHCOR^{23}$,
(j) —$CH_2SO_2NHCONHR^{23}$, or
(k) —$CO_2H$;
$R^{2a}$ and $R^{2b}$ are each independently:
(a) hydrogen,
(b) —Cl, —Br, —I, or —F
(c) —$CF_3$,
(d) $C_1$-$C_4$-alkyl, or
(e) $C_1$-$C_4$-alkoxy;
$R^{3a}$ is
(a) —H,
(b) —Cl, —Br, —I, or —F,
(c) $C_1$-$C_6$-alkyl,
(d) $C_1$-$C_6$-alkoxy, or
(e) $C_1$-$C_6$-alkoxy-$C_1$-$C_4$-alkyl;
$R^{3b}$ is
(a) —H,
(b) —Cl, —Br, —I, or —F,
(c) $C_1$-$C_6$-alkyl,
(d) $C_1$-$C_5$-alkylcarbonyloxy,
(e) $C_3$-$C_6$-cycloalkyl
(f) $C_1$-$C_6$-alkoxy, or
(g) $CF_3$;
$R^4$ is H, $C_1$-$C_6$ alkyl, —$CH_2$-aryl or aryl wherein aryl is phenyl or naphthyl unsubstituted or substituted with one or two substituents selected from the group consisting of: —Cl, —Br, —I, —F, $C_1$-$C_4$-alkyl, $C_1$-$C_4$-alkoxy, $NO_2$, $CF_3$, $C_1$-$C_4$-alkylthio, —OH, —$NH_2$, —$CO_2H$, —$CO_2$—$C_1$-$C_4$-alkyl, —CN and —$NHCOR^9$;
$R^5$ is H or —$CH(R^4)$—O—CO—$R^{4a}$, wherein $R^{4a}$ is $C_1$-$C_6$-alkyl, aryl or —$CH_2$-aryl;
E is a single bond, —$NR^{13}(CH_2)_s$—, —$S(O)_x(CH_2)_s$— where x is 0 to 2 and s is 0 to 5, —CH(OH)—, —$O(CH_2)_s$—, —CO—;
$R^6$ is
(a) phenyl, unsubstituted or substituted with 1 or 2 substituents selected from the group consisting of Cl, Br, I, F, —O—$C_1$-$C_4$-alkyl, $C_1$-$C_4$-alkyl, —$NO_2$, —$CF_3$, —$SO_2NR^9R^{10}$, —S—$C_1$-$C_4$-alkyl, —OH, —$NH_2$, $C_3$-$C_7$-cycloalkyl, and $C_3$-$C_{10}$-alkenyl;
(b) $C_1$-$C_6$-alkyl, $C_2$-$C_6$-alkenyl or $C_2$-$C_6$-alkynyl each of which is unsubstituted or substituted with one or more substituents selected from the group consisting of: aryl, $C_3$-$C_7$-cyclo-alkyl, Cl, Br, I, F, —OH, —O—$C_1$-$C_4$-alkyl, —$NH_2$, —NH($C_1$-$C_4$-alkyl), —N($C_1$-$C_4$-alkyl)$_2$, —NH—$SO_2R^4$, —$COOR^4$, —$SO_2NHR^9$, and —S—$C_1$-$C_4$-alkyl;
(c) mono-, di-, tri- or polyfluoro-$C_1$-$C_5$-alkyl;

(d) $C_3$-$C_7$-cycloalkyl, unsubstituted or substituted with one or more substituents selected from the group consisting of $C_1$-$C_4$-alkyl, O—$C_1$-$C_4$-alkyl, S—$C_1$-$C_4$-alkyl, OH, perfluoro-$C_1$-$C_4$-alkyl, Cl, Br, F, and I; or (e) $C_3$-$C_7$-cycloalkyl-$C_1$-$C_3$-alkyl, wherein the cycloalkyl is unsubstituted or substituted as in (e) above;

A is =O, =S or =$NR^{21}$;

B is
(a) H provided A is not $NR^{21}$;
(b) $C_1$-$C_{10}$-alkyl;
(c) substituted $C_1$-$C_{10}$-alkyl in which one or more substituent(s) is selected from the group consisting of:
(1) I, Br, Cl, or F,
(2) hydroxy,
(3) $C_1$-$C_{10}$-alkoxy,
(4) $C_1$-$C_5$-alkoxycarbonyl,
(5) $C_1$-$C_4$-alkylcarbonyloxy,
(6) $C_3$-$C_8$-cycloalkyl,
(7) phenyl, naphthyl or biphenyl,
(8) substituted phenyl, naphthyl or biphenyl in which the substituents are $V_1$, $V_2$, $V_3$, $V_4$ and $V_5$,
(9) $C_1$-$C_{10}$-alkyl-S(O)$_p$ in which p is 0 to 2,
(10) $C_3$-$C_8$-cycloalkyl-S(O)$_p$,
(11) phenyl-S(O)$_p$,
(12) substituted phenyl-S(O)$_p$ in which the substituents are $V_1$-$V_5$,
(13) oxo,
(14) carboxy,
(15) $NR^9R^9$,
(16) $C_1$-$C_5$-alkylaminocarbonyl,
(17) di($C_1$-$C_5$-alkyl)aminocarbonyl,
(18) cyano,
(19) —$OCONR^{21}R^{22}$,
(20) —$NR^{21}COR^{22}$,
(21) —$NR^{21}CO_2R^{22}$, or
(22) —$NR^{21}CONR^{21}R^{22}$,
(d) $C_2$-$C_{10}$-alkenyl,
(e) $C_2$-$C_{10}$-alkynyl,
(f) $C_3$-$C_8$-cycloalkyl,
(g) substituted $C_3$-$C_8$-cycloalkyl or substituted $C_3$-$C_8$-cycloalkyl-$C_1$-$C_4$-alkyl having one or more substituents selected from the group consisting of:
(1) Cl, Br, F, or I,
(2) hydroxy,
(3) $C_1$-$C_6$-alkyl,
(4) $C_1$-$C_6$-alkoxy,
(5) $C_1$-$C_4$-alkylcarbonyloxy,
(6) $C_1$-$C_5$-alkoxycarbonyl,
(7) carboxy,
(8) oxo,
(9) $C_1$-$C_5$-alkylaminocarbonyl,
(10) di($C_1$-$C_5$-alkyl)aminocarbonyl,
(11) $C_1$-$C_4$-alkylcarbonyl,
(12) phenyl, naphthyl or biphenyl,
(13) substituted phenyl, naphthyl or biphenyl in which the substituents are $V_1$, $V_2$, $V_3$, $V_4$ and $V_5$,
(14) —$NR^{21}COR^{22}$,
(15) —$NR^{21}CO_2R^{22}$,
(16) —$OCONR^{21}R^{22}$, and
(17) —CN;
(h) phenyl, naphthyl or biphenyl,
(i) substituted phenyl, naphthyl or biphenyl in which the substituents are $V_1$, $V_2$, $V_3$, $V_4$ and $V_5$, (j) phenyl—(CH$_2$)$_r$—(Q)$_{cl}$—(CH$_2$)$_r$—,
(k) substituted phenyl—(CH$_2$)$_r$—(Q)$_c$—(CH$_2$)$_r$— in which the phenyl group is substituted with $V_1$, $V_2$, $V_3$, $V_4$ and $V_5$,

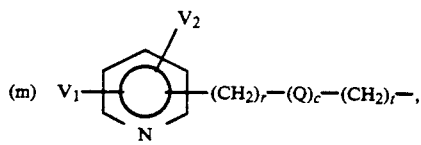

(m)

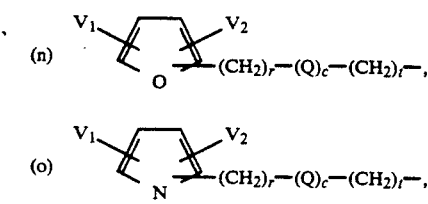

(n)

(o)

$R^9$ is H, $C_1$-$C_5$-alkyl, aryl or —CH$_2$-aryl;
$R^{10}$ is H, $C_1$-$C_4$-alkyl, or
$R^9$ and $R^{10}$ together can be —(CH$_2$)$_m$— where m is 3-6;
$R^{11}$ is H, $C_1$-$C_6$-alkyl, $C_2$-$C_4$-alkenyl, $C_1$-$C_4$-alkoxy-$C_1$-$C_4$-alkyl, or —CH$_2$—C$_6$H$_4$R$^{20}$;
$R^{12}$ is —CN, —NO$_2$ or —CO$_2$R$^4$;
$R^{13}$ is H, $C_2$-$C_4$-alkanoyl, $C_1$-$C_6$-alkyl, allyl, $C_3$-$C_6$-cycloalkyl, phenyl or benzyl;
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl, hydroxy;
$R^{16}$ is H, $C_1$-$C_6$-alkyl, $C_3$-$C_6$-cycloalkyl, phenyl or benzyl;
$R^{17}$ is —$NR^9R^{10}$, —$OR^{10}$, —NHCONH$_2$, —NHCSNH$_2$, —NHSO$_2$CF$_3$,

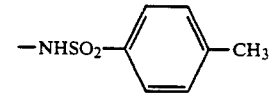

or

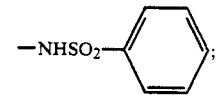

$R^{18}$ and $R^{19}$ are independently $C_1$-$C_4$-alkyl or taken together are —(CH$_2$)$_q$— where q is 2 or 3;
$R^{20}$ is H, —NO$_2$, —NH$_2$, —OH or —OCH$_3$;
$R^{21}$ is
(a) H,
(b) phenyl, unsubstituted or substituted with 1 or 2 substituents selected from the group consisting of: Cl, Br, I, F, —O—$C_1$-$C_4$-alkyl, $C_1$-$C_4$-alkyl, —NO$_2$, —CF$_3$, —SO$_2$NR$^9$R$^{10}$, —S—$C_1$-$C_4$-alkyl, —OH, —NH$_2$, —COOR$^4$, $C_3$-$C_7$-cycloalkyl and $C_3$-$C_{10}$-alkenyl;
(c) $C_1$-$C_6$-alkyl, $C_2$-$C_6$-alkenyl or $C_2$-$C_6$-alkynyl each of which is unsubstituted or substituted with one or more substituents selected from the group consisting of aryl, $C_3$-$C_7$-cyclo-alkyl, Cl, Br, I, F, —OH, —O—$C_1$-$C_4$-alkyl, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and —S—$C_1$-$C_4$-alkyl;

(d) $C_3$-$C_7$-cycloalkyl, unsubstituted or substituted with one or more substituents selected from the group consisting of: $C_1$-$C_4$-alkyl, —O—$C_1$-$C_4$-alkyl, —S—$C_1$-$C_4$-alkyl, —OH, —COOR$^4$, $C_1$-$C_4$-perfluoroalkyl, Cl, Br, F, and I, or
(e) ($C_1$-$C_4$)-perfluoroalkyl;

$R^{22}$ is $R^{21}$ excluding H;

$R^{23}$ is
(a) aryl,
(b) heteroaryl, wherein heteroaryl is defined as unsubstituted, monosubstituted or disubstituted pyridine, wherein the substituents are selected from the group consisting of —OH, —SH, $C_1$-$C_4$-alkyl, $C_1$-$C_4$-alkoxy, —CF$_3$, Cl, Br, F, I, —NO$_2$ —CO$_2$H, —CO$_2$—$C_1$-$C_4$-alkyl, —NH$_2$, —NH($C_1$-$C_4$-alkyl) and —N($C_1$-$C_4$-alkyl)$_2$;
(c) $C_3$-$C_7$-cycloalkyl optionally substituted with one or more substituents selected from the group consisting of $C_1$-$C_4$-alkyl, —O—$C_1$-$C_4$-alkyl, —S—$C_1$-$C_4$-alkyl, —OH, —COOR$^4$, perfluoro-$C_1$-$C_4$-alkyl, Cl, Br, F, and I;
(d) $C_1$-$C_8$-alkyl unsubstituted or substituted with one or two substituents selected from the group consisting of: aryl, heteroaryl, —OH, —SH, $C_1$-$C_4$-alkyl, $C_2$-$C_4$-alkenyl, $C_2$-$C_4$-alkynyl, —O($C_1$-$C_4$-alkyl), S($C_1$-$C_4$-alkyl), —$C_3$-$C_8$-cycloalkyl, —CF$_3$, Cl, Br, F, I, —NO$_2$, —CO$_2$H, —CO$_2$—$C_1$-$C_4$-alkyl, —PO$_3$H, —PO(OH)(O—$C_1$-$C_4$-alkyl), —PO(OR$^4$)(R$^9$), —NH$_2$, —NH($C_1$-$C_4$-alkyl), —N($C_1$-$C_4$-alkyl)$_2$, —NH-aryl, —N(aryl)$_2$, —NR$^4$COR$^{22}$, —CONR$^4$R$^{22}$, —OCONR$^4$R$^{22}$, SO$_2$NR$^4$R$^{22}$, —NR$^4$SO$_2$R$^{22}$,
(e) polyfluoro-$C_1$-$C_4$-alkyl, or
(f) —NR$^{21}$R$^{21}$;

X is
(a) a single bond,
(b) —CO—,
(c) —O—,
(d) —S—, (e) 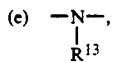

(f) 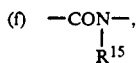

(g) 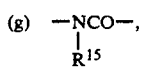

(h) —OCH$_2$—,
(i) —CH$_2$O—
(j) —SCH$_2$—,
(k) —CH$_2$S—,
(l) —NHC(R$^9$)(R$^{10}$)—,
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,
(v) 1,1-dimethylcyclopropyl or 1,2-dimethylcyclopropyl, (w) 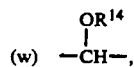

(x) 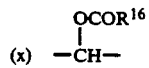

(y) 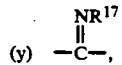

or (z) 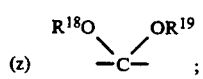 ;

Q is —C(O)—, —S—, —O— or —NR$^4$;

c is 0 or 1;

r and t are 0 to 2;

$V_1$, $V_2$, $V_3$, $V_4$ and $V_5$ are each independently selected from:
(a) H,
(b) $C_1$-$C_5$-alkoxy,
(c) $C_1$-$C_5$-alkyl,
(d) hydroxy,
(e) $C_1$-$C_5$-alkyl-S(O)$_p$,
(f) —CN,
(g) —NO$_2$,
(h) —NR$^9$R$^{10}$,
(i) $C_1$-$C_5$-alkyl-CONR$^9$R$^{10}$,
(j) —CONR$^9$R$^{10}$,
(k) —CO$_2$R$^9$,
(l) $C_1$-$C_5$-alkyl-carbonyl,
(m) CF$_3$,
(n) I, Br, Cl, F,
(o) hydroxy-$C_1$-$C_4$-alkyl-,
(p) carboxy-$C_1$-$C_4$-alkyl-,
(q) —NH—SO$_2$CF$_3$,
(r) aryl,
(s) $C_1$-$C_5$-alkyl-CO$_2$R$^9$,
(t) aryloxy,
(u) aryl-$C_1$-$C_3$-alkoxy,
(v) aryl-$C_1$-$C_3$-alkyl,
(w) carboxyphenyl,
(x) —(CH$_2$)$_r$OCOR$^{22}$,
(y) —(CH$_2$)$_r$OCONR$^{21}$R$^{22}$,
(z) —(CH$_2$)$_t$NR$^{21}$COR$^{22}$,
(aa) —(CH$_2$)$_t$NR$^{21}$CO$_2$R$^{22}$, or
(bb) —(CH$_2$)$_t$NR$^{21}$CONR$^{23}$R$^{22}$;

u is 1 or 2; and

Z is O, NR$^{13}$ or S.

* * * * *